US006894116B2

(12) United States Patent
Lai et al.

(10) Patent No.: US 6,894,116 B2
(45) Date of Patent: May 17, 2005

(54) S,S'-BIS-(α, α'—DISUBSTITUTED—α"—ACETIC ACID)—TRITHIOCARBONATES AND POLYMERS THEREOF FOR TOUGHENING THERMOSETTING RESINS

(75) Inventors: John Ta-Yuan Lai, Broadview Heights, OH (US); Carole Angele Lepilleur, Akron, OH (US); Carl Duane Weber, Copley, OH (US); David Richard Egan, Stow, OH (US); Deborah Susan Filla, Twinsburg, OH (US)

(73) Assignee: Noveon IP Holdings Corp., Cleveland, OH (US)

( * ) Notice: Subject to any disclaimer, the term of this patent is extended or adjusted under 35 U.S.C. 154(b) by 0 days.

(21) Appl. No.: 10/219,403

(22) Filed: Aug. 15, 2002

(65) Prior Publication Data

US 2003/0187138 A1 Oct. 2, 2003

Related U.S. Application Data

(63) Continuation-in-part of application No. 09/505,749, filed on Feb. 16, 2000, now Pat. No. 6,596,899.

(51) Int. Cl.[7] ........................... C08F 8/00; C08F 283/00; C08L 63/00; C08G 59/14; C07C 329/00

(52) U.S. Cl. ........................ 525/107; 525/525; 525/535; 528/419; 549/561; 549/562; 558/243

(58) Field of Search ................................. 525/107, 525, 525/535; 528/419; 549/561, 562; 562/426, 594; 558/243

(56) References Cited

U.S. PATENT DOCUMENTS

| | | | |
|---|---|---|---|
| 2,858,292 A | * 10/1958 | Swart et al. ............... | 260/45.8 |
| 3,285,945 A | 11/1966 | Wember ................... | 260/429.9 |
| 3,285,949 A | 11/1966 | Siebert ..................... | 260/465.4 |
| 3,770,698 A | 11/1973 | Riew ............................ | 260/47 |
| 3,928,491 A | 12/1975 | Waters ....................... | 260/836 |
| 3,992,432 A | 11/1976 | Napier et al. ............. | 260/465.1 |
| 4,769,419 A | 9/1988 | Dawdy ....................... | 525/111 |
| 5,055,515 A | 10/1991 | Backderf .................... | 524/533 |
| 5,140,068 A | 8/1992 | Siebert et al. .............. | 525/108 |
| 5,157,077 A | 10/1992 | Siebert et al. .............. | 525/108 |
| 5,198,510 A | 3/1993 | Siebert et al. .............. | 525/531 |
| 5,258,445 A | 11/1993 | Sperk, Jr. et al. .......... | 524/597 |
| 5,280,068 A | 1/1994 | Siebert et al. .............. | 525/108 |
| 5,312,956 A | 5/1994 | Bertsch ....................... | 558/409 |
| 5,385,963 A | 1/1995 | McBain et al. ............. | 523/406 |
| 5,604,084 A | * 2/1997 | Grzeskowiak et al. ...... | 430/567 |
| 6,153,705 A | 11/2000 | Corpart et al. ............. | 525/244 |
| 6,380,335 B1 | 4/2002 | Charmot et al. ........... | 526/220 |
| 6,395,850 B1 | 5/2002 | Charmot et al. ........... | 526/220 |

FOREIGN PATENT DOCUMENTS

| | | |
|---|---|---|
| EP | 0704460 | 4/1996 |
| WO | 98/01478 | 1/1998 |
| WO | 99/05099 | 2/1999 |
| WO | 99/31144 | 6/1999 |
| WO | 99/35177 | 7/1999 |

OTHER PUBLICATIONS

Encyclopedia of Polymer Science and Engineering vol. 4, John Wiley & Sons, Inc. p. 543 © 1986.*

G.P. Moss, P.A.S. Smith, D. Tavernier, Pure and Applied Chemistry, vol. 67, pp. 1307–1375 (1995).*

Hawley's Condensed Chemical Dictionary, 12th ed., Richard J. Lewis, Sr. , © 1993 by Van Nostrand Reinhold. p. 594.*

Concise Chemical Dictionary, edited by Drs. Hans–Dieter Jakubke and Hans Jeschkeit, © 1993 by Walter de Gruyter & Co., p. 490.*

McGraw–Hill Dictionary of Chemical Terms, 3rd ed. edited by Sybil P. Parker, © 1984 McGraw–Hill, Inc., p. 200.*

World Polymer Congress, 37th International Symposium on Macromolecules, Jul. 12–17, 1998, Gold Coast, Australia.

"Living Free–Radical Polymerization by Reversible Addition–Fragmentation Chain Transfer: The RAFT Process", John Chiefari, eta l., CSIRO *Molecular Science, Bag 10*, Clayton South. Clayton, Victoria 3169, Australia, Received Mar. 27, 1998, Revised Manuscript Received Jun. 10, 1998.

"The Synthesis of Organic Trethiocarbonates[1]", H.C. Godt, Jr., and R.E. Wann, *Journal of Organic Chemistry*, 26, 4047 (1961).

"Phase–Transfer Synthesis of Symmetrical and Unsymmetrical Dialkyl Trithiocarbonates", Iacopo Degani, et al, Synthesis, p. 894 (1986).

"A New Form of Controlled Growth Free Radical Polymerization", Julia Kristina, et al., CSIRO, Division of Chemicals and Polymers, *Macromol, Symp.* III, 13–23 (1996).

"One Pot Phase Transfer Synthesis of Trithiocarbonates from Carbon Disulphide and Alkyl Halides", Albert W.M. Lee, et al, *Synthetic Comm.* 18 (13), 1531 (1988).

"A Novel One–step Synthesis of Symmetrical Dialkyl Trithicarbonates", Man–kit Leung, et al, *Journal of Chemical Research* (S), 1995, 478–479.

"Direct Synthesis of Double Hydrophilic Statistical di– and Triblock Copolymers Comprised of Acrylamide and Acrylic Acid Units via the MADIX Process", Daniel Taton, et al, Macromol, Rapid Commun, 22, No. 18 (2001).

(Continued)

Primary Examiner—Richard L. Raymond
Assistant Examiner—Zachary C. Tucker
(74) Attorney, Agent, or Firm—Thoburn T. Dunlap; Hudak, Shunk & Farine Co., L.P.A.

(57) ABSTRACT

A toughener comprising a trithiocarbonate polymer having an epoxy end group is described which is utilized with various thermosettable polymers such as epoxy, polyurethane, and the like. A toughened composition is made by curing the thermosettable polymer and the toughener utilizing various curing agents.

22 Claims, No Drawings

OTHER PUBLICATIONS

"Living Radical Polymerization with Reversible Addition—Fragmentation Chain Transfer (RAFT Polymerization) Using Ditriocarbamates as Chain Transfer Agents", Roshan T.A. mayadunne, et al., CSIRO *Molecular Science, Bag 10*, Clayton, South, Victoria 3169, Australia, Received May 3, 1999; Revised Manuscript Received Aug. 9, 1999.

"Dithiocarbamates as universal reversible addition–fragmentation chain transfer agents", M. Destarac, et al, Macromol. Rapid Commun., 21, No. 15, (2000).

* cited by examiner

S,S'-BIS-(α, α'— DISUBSTITUTED— α"— ACETIC ACID)— TRITHIOCARBONATES AND POLYMERS THEREOF FOR TOUGHENING THERMOSETTING RESINS

CROSS REFERENCE

This patent application is a continuation-in-part application based on U.S. application Ser. No. 09/505,749 now U.S. Pat. No. 6,596,899 filed Feb. 16, 2000 for S,S'-Bis-(α,α'—Disubstituted—α"—Acetic Acid)—Trithiocarbonates And Derivatives As Initiator—Chain Transfer Agent—Terminator For Controlled Radical Polymerizations And The Process For Making The Same.

FIELD OF THE INVENTION

The present invention relates to s,s'-bis-(α,α'—disubstituted—α"—acetic acid)—trithiocarbonates and derivatives thereof, as well as a process for making the same. Such compounds can be reacted with monomers to form acrylate repeat units within the compound. Subsequently, functional end groups can be added thereto such as epoxy, vinyl, or hydroxyl groups. The acrylated polymer, which has inherent oxidative and ultraviolet stability properties, contains end groups such as epoxy and can be utilized as toughening agents for epoxy resins.

BACKGROUND OF THE INVENTION

Although several members of the class of organic thiocarbonates have been known for many years and various routes have been employed for their synthesis, the s,s'-bis-(α,α'—disubstituted—α"—acetic acid)—trithiocarbonate compounds of the present invention have not been disclosed. Trithiocarbonate compounds have been claimed for various applications, such as pesticides for agriculture, and also as lubricating oil additives.

Traditional methods of producing block copolymers, such as by living polymerization or the linking of end functional polymers, suffer many disadvantages, such as the restricted type monomers which can be utilized, low conversion rates, strict requirements on reaction conditions, and monomer purity. Difficulties associated with end linking methods include conducting reactions between polymers, and problems of producing a desired pure end functional polymer. The s,s'-bis-(α,α'—disubstituted—α"—acetic acid)—trithiocarbonate compounds of the present invention can alleviate the above noted problems and difficulties when utilized in free radical polymerizations.

The prior art WO98/01478 reference discloses the use of thiocarbonates to conduct living free radical polymerizations. The reference is limited to alkyl and benzyl functional groups, and is unable to make any aryl or carboxylic acid substituted trithiocarbonates with general methods known to the art. *Synthesis*, p 894 (1986), *J. Chemical Research* (Synopsis), p478 (1995), and *Synthetic Communications*, Vol. 18, p 1531 (1988). We have also found the conversion for the dibenzyl derivatives disclosed in their example 26 to be very slow compared to the present invention when polymerizing acrylate, as can be seen in the Example section of this application.

The ability of a brittle or thermoset epoxy resin to absorb energy without catastrophic failure can be increased through flexibilizing or toughening. Such flexibilizing and toughening may be accomplished by reacting or compounding the epoxy resin with an elastomer thereby enhancing the resin system's ability to resist mechanical and thermal stress. Such elastomers are known and include reactive liquid polymers such as carboxyl-terminated polymers as exemplified by U.S. Pat. No. 3,285,949, and amine-terminated polymers as disclosed in U.S. Pat. No. 3,823,107. It is also known that liquid carboxyl-terminated polymers have the advantage of a material which is pourable and castable at room temperature and because of the reactive functional chain ends it can be further reacted at elevated temperatures by the addition of polyamines or diepoxies to form the liquid diamine or diepoxy terminated polymers. Such liquid elastomers have found a wide variety of utility, but are particularly useful as toughening agents in sealants, caulk, adhesive and potting epoxy resin systems.

U.S. Pat. No. 3,285,945 relates to the production of liquid, carboxyl-terminated polymers, and more particularly relates to the use of a certain class of catalysts in combination with a particular solvent for the production of difunctional carboxyl-terminated butadiene polymers.

U.S. Pat. No. 3,770,698 relates to phenol terminated elastomers prepared by reacting carboxyl terminated polymers of dienes with diphenols such as bisphenol A, so that the carboxyl groups become part of the molecular chain and phenolic hydroxyls become end groups.

SUMMARY OF THE INVENTION

The present invention relates to s,s'-bis-(α,α'—disubstituted—α"—acetic acid)—trithiocarbonates which have the general formula:

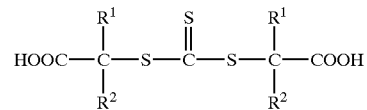

where $R^1$ and $R^2$ are set forth below, to derivatives thereof, and to a process for making the same.

The s,s'-bis-(α,α'—disubstituted—α"—acetic acid) trithiocarbonate compounds can generally be formed from carbon disulfide, a haloform, and a ketone in a strong base, such as sodium hydroxide, followed by acidification. The s,s'-bis-(α,α'—disubstituted—α"—acetic acid) trithiocarbonate compounds can be reacted with various monomers such as acrylates whereby they are incorporated into the polymer chain or backbone. Such acrylate containing trithiocarbonate polymers are then reacted with an epoxy which adds onto the carboxyl end portion and forms an epoxy end group. Subsequently, such epoxy terminated polymers can be used to toughen various thermosetting polymers such as epoxy resins.

DETAILED DESCRIPTION OF THE INVENTION

Preparation of s,s'-bis-(α,α'—disubstituted—α"— acetic acid)—trithiocarbonate

The s,s'-bis-(α,α'—disubstituted—α"—acetic acid)—trithiocarbonate and derivatives prepared by the processes disclosed later herein generally can be described by the formula:

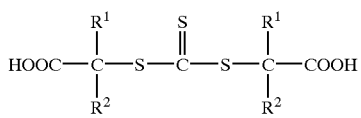

wherein $R^1$ and $R^2$, independently, can be the same or different, and can be linear or branched alkyls having from 1 to about 6 carbon atoms, or a $C_1$ to about $C_6$ alkyl having one or more substituents, or one or more aryls or a substituted aryl group having 1 to 6 substituents on the aryl ring, where the one or more substituents, independently, comprise an alkyl having from 1 to 6 carbon atoms; or an aryl; or a halogen such as fluorine or chlorine; or a cyano group; or an ether having a total of from 2 to about 20 carbon atoms such as methoxy, or hexanoxy; or a nitro; or combinations thereof. Examples of such compounds include s,s'-bis-2-methyl-2-propanoic acid-trithiocarbonate and s,s'-bis-(2-phenyl-2-propanoic acid)-trithiocarbonate. $R^1$ and $R^2$ can also form or be a part of a cyclic ring having from 5 to about 12 total carbon atoms. $R^1$ and $R^2$ are preferably, independently, methyl or phenyl groups.

The abbreviated reaction formula for the formation of the s,s'-bis-($\alpha,\alpha'$—disubstituted—$\alpha''$—acetic acid)—trithiocarbonates of the present invention can be generally written as follows:

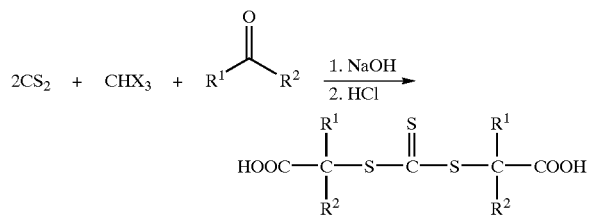

The process utilized to form the s,s'-bis-($\alpha,\alpha'$—disubstituted—$\alpha''$—acetic acid)—trithiocarbonate compounds of the present invention is generally a multi-step process and includes combining the carbon disulfide and a base whereby an intermediate trithio structure is formed, see I, II, III, and IV. Ketone can serve as solvent for the carbon disulfide/base reaction and thus can be added in the first step of the reaction. In the second step of the reaction, the haloform, or haloform and ketone, or a $\alpha$-trihalomethyl-$\alpha$-alkanol are added to the trithio intermediate mixture and reacted in the presence of additional base, see V, VI, and VII. The formed reaction product, see IX, is subsequently acidified, thus completing the reaction and forming the above described s,s'-bis-($\alpha,\alpha'$—disubstituted—$\alpha''$—acetic acid)—trithiocarbonate compound, see X.

The reaction is carried out at a temperature sufficient to complete the interaction of the reactants so as to produce the s,s'-bis-($\alpha,\alpha'$—disubstituted—$\alpha''$—acetic acid)—trithiocarbonate compound in a desired time. The reaction can be carried out at any temperature within a wide range from about the freezing point of the reaction mass to about the reflux temperature of the solvent. The reaction temperature is generally from about minus 15° C. to about 80° C., desirably from about 0° C. to about 50° C., and preferably from about 15° C. to about 35° C., with room temperature being preferred. The reaction can be performed at atmospheric pressure. The reaction time depends upon several factors, with the temperature being most influential. The reaction is generally complete within 20 hours and preferably within 10 hours.

A phase transfer catalyst is preferably utilized if a solvent is used in the reaction. Examples of solvents are set forth herein below. The ketone utilized in the reaction may double as a solvent, and therefore no catalyst usually is needed. The amount of phase transfer catalyst, when utilized in the present invention, is generally from about 0.1 mole percent to about 10 mole percent, desirably from about 0.5 mole percent to about 5 mole percent and preferably from about 2 mole percent to about 4 mole percent per mole of carbon disulfide. The phase transfer catalysts can be polyether, and/or an onium salt including a quaternary or tertiary organic compound of a group VA or VIA element of the Periodic Table and salts thereof. Most preferred are quaternary amines, and salts thereof.

The "Onium salt" catalyst, more particularly refer to tertiary or quaternary amines and salts, generally used in the phase transfer catalysis of heterogeneous reaction in immiscible liquids. The general requirement for the onium salt chosen is that it be soluble in both the organic and aqueous phases, when these two liquid phases are present, and usually a little more soluble in the organic phase than the aqueous phase. The reaction will also proceed with a phase transfer catalyst when there is only a single organic liquid phase present, but such a reaction is less preferable than one in which both aqueous and organic liquid phases are present. A wide variety of onium salts is effective in this ketoform synthesis.

The onium salts include the well-known salts, tertiary amines and quaternary compounds of group VA elements of the Periodic Table, and some Group VIA elements such as are disclosed in the U.S. Pat. No. 3,992,432 and in a review in Angewandte Chemie, International Edition in English, 16 493–558 (August 1977). Discussed therein are various anion transfer reactions where the phase transfer catalyst exchanges its original ion for other ions in the aqueous phase, making it possible to carry our chemistry there with the transported anion, including OH-ions.

The onium salts used in this synthesis include one or more groups having the formula $(R_nY)^+ X^-$, wherein Y is either a pentavalent ion derived from an element of Group VA, or a tetravalent ion derived from an element of Group VIA; R is an organic moiety of the salt molecule bonded to Y by four covalent linkages when Y is pentavalent, and three covalent linkages when Y is tetravalent; $X^-$ is an anion which will dissociate from the cation $(R_nY)^+$ in an aqueous environment. The group $(R_nY)^+ X^-$ may be repeated as in the case of dibasic quaternary salts having two pentavalent Group VA ions substituted in the manner described.

The preferred onium salts for use in the invention have the formula $$(R^AR^BR^CR^DY^+)X^-$$

wherein Y is N or P, and $R^1$–$R^4$ are monovalent hydrocarbon radicals preferably selected from the group consisting of alkyl, alkenyl, aryl, alkaryl, aralkyl, and cycloalkyl moieties or radicals, optionally substituted with suitable heteroatom-containing functional groups. The onium salts are generally selected to be less preferentially less soluble in the less polar of the two distinct liquid phases. Any of the salts disclosed in the U.S. Pat. No. 3,992,432 will be found effective, but most preferred are those in which the total number of carbon atoms in $R^A, R^B, R^C$, and $R^D$ cumulatively range from about 13 to about 57, and preferably range from about 16 to about 30. Most preferred onium salts have Y=N, and hydrocarbon radicals where $R^A$ is $CH_3$, and $R^B$, $R^C$, and $R^D$ are each selected from the group consisting of n-$C_2H_5$, n-$C_4H_5$; n-$C_5H_{11}$; mixed $C_5H_{17}$; n-$C_{12}H_{29}$; n-$C_{18}H_{37}$; mixed $C_8$–$C_{10}$ alkyl; and the like. However. $R^A$ may also be selected from $C_2H_5$, n-$C_3H_7$ and n-$C_4H_9$ benzyl.

Various counterions may be used, including Cl⁻, Br⁻, I⁻, $NO_3^-$, $SO_4^{-2}$, $HSO_4^-$ and $CH_2CO_2^-$. Most preferred is Cl⁻.

The tertiary amines or triamines useful as phase transfer catalysts in this synthesis include the alkyl amines and the aryidialkylamines, exemplified by tributylamine and phenyldibutylamine respectively, which are commonly available, wherein each alkyl may have from 1 to about 16 carbon atoms.

The polyethers useful as catalysts in this synthesis include cyclic polyethers such as the crown ethers, disclosed in *Agenwandte Chemie*, supra, and acyclic polyethers having the formula $$R—O—R^E$$

wherein R and $R^E$ are, independently, alkyls having from 1 to about 16 carbon atoms, or alkyl containing substituted functional groups such as hydroxy, sulfur, amine, ether, etc. Most preferred acyclic polyethers have the formula $$R—(OCH_2CH_2), OR"$$

wherein

R is an alkyl having from 1 to about 16 carbon atoms

R" is an alkyl having from 1 to about 16 carbon atoms, or H, and r is an integer in the range from 0 to about 300.

Most preferred are commonly available polyethers such as: tetraethylene glycol dimethyl ether; polyethylene oxide (mol wt. About 5000); poly(ethylene glycol methyl ether); 1,2-dimethoxyethane; diethyl ether, and the like.

Polyether catalysts are especially desirable in this ketoform synthesis because they are directive so as to produce a preponderance of the desired symmetrically substituted isomer, in a reaction which is remarkably free of undesirable byproducts, which reaction proceeds with a relatively mild exotherm so that the reaction is controllable.

The organic solvent can be any solvent in which the reactants are soluble and include hydrohalomethylenes, particularly hydrochloromethylenes, sulfolane, dibutyl ether, dimethyl sulfone, diisopropyl ether, di-n-propyl ether, 1,4-dioxane, tetrahydrofuran, benzene, toluene, hexane, carbon tetrachloride, heptane, mineral spirits and the like. Most preferred solvents are heptanes and mineral spirits. Solvent is generally utilized in an amount generally from about 10 to about 500 percent and preferably from about 50 percent to about 200 percent based on the total weight of the reactants.

Insofar as the reactive components are concerned, any of various ketones having the general formula:

$$R^1—\overset{\overset{O}{\|}}{C}—R^2$$

can be employed in the synthesis, wherein $R^1$ and $R^2$ are described herein above. As carbon disulfide is the controlling agent in the reaction, the ketone is generally used in an amount from about 110 mole percent to about 2,000 mole percent per mole of carbon disulfide. When the ketone is used as a solvent, it is generally utilized in an amount of from about 150 mole percent to about 300 mole percent, and preferably from about 180 mole percent to about 250 mole percent per mole of carbon disulfide.

The alkali bases suitable for use in the synthesis of the present invention include, but are not limited to, sodium hydroxide and potassium hydroxide. The base is utilized in an amount generally from about 5 times to about 15 times the number of moles of carbon disulfide and preferably from about 6 to about 10 times the number of moles of carbon disulfide utilized in the reaction.

The acids used in the acidification step include, but are not limited to, hydrochloric acid, sulfuric acid, phosphoric acid, etc. The acids are utilized in amounts suitable to make the aqueous solution acidic.

The haloform of the present invention has the general formula $CHX_3$ wherein X is, independently, chlorine or bromine. The amount of haloform used in the present invention is generally from about 110 mole percent to about 2000 mole percent, desirably from about 150 mole percent to about 300 mole percent, and preferably 180 mole percent to about 250 mole percent per mole of carbon disulfide. Examples of haloforms include, but are not limited to, chloroform and bromoform, and chloroform is the preferred haloform of the present invention.

Alternatively, instead of adding both a haloform and a ketone, to the reaction mixture, an α-trihalomethyl-α-alkanol can be substituted therefore. The amount of α-trihalomethyl-α-alkanol utilized in the reaction generally is from about 110 mole percent to about 2000 mole percent, desirably is from about 150 mole percent to about 300 mole percent, and preferably is from about 180 mole percent to about 250 mole percent per mole of carbon disulfide. The general formula of the α-trihalomethyl-α-alkanol is generally represented as follows:

$$\underset{R^1 \quad R^2}{\overset{HO \quad CX_3}{\diagdown C \diagup}}$$

wherein X, $R^1$ and $R^2$ are defined above.

While not wishing to be limited to any particular mechanism, it is believed that the specific mechanism for the reaction process is as follows:

Initially, the carbon disulfide and sodium hydroxide are reacted.

$$CS_2 + 2NaOH \quad\quad\quad\quad\quad\quad\quad\quad I$$

$$\downarrow$$

$$Na^+—O—\overset{\overset{S}{\|}}{C}—S—Na^+ + H_2O \quad\quad II$$

$$\downarrow CS_2$$

$$Na^+—O—\overset{\overset{S}{\|}}{C}—S—\overset{\overset{S}{\|}}{C}—S—Na^+ \quad\quad III$$

$$\downarrow 2\,NaOH$$

$$Na^+—O—\overset{\overset{S}{\|}}{C}—O—Na^+ + Na^+—S—\overset{\overset{S}{\|}}{C}—S—Na^+ + H_2O \quad IV$$

(trithio intermediate)

In the subsequent step of the reaction, the chloroform is reacted with the ketone as follows:

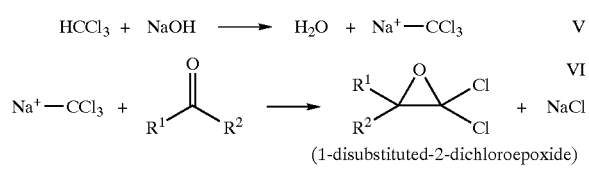

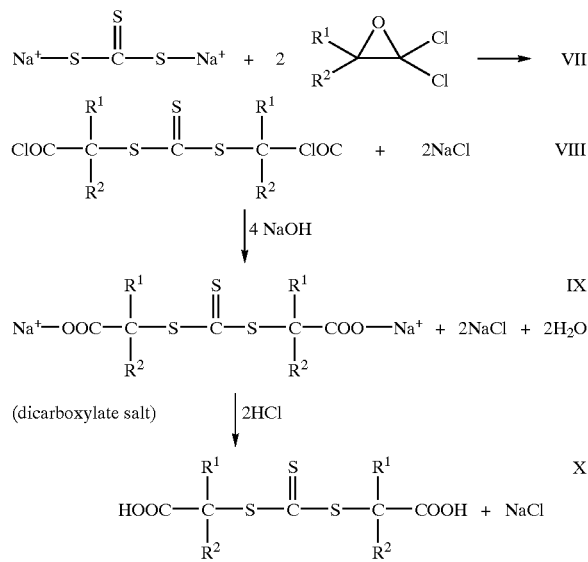

(dicarboxylate salt)

The overall reaction is as follows:

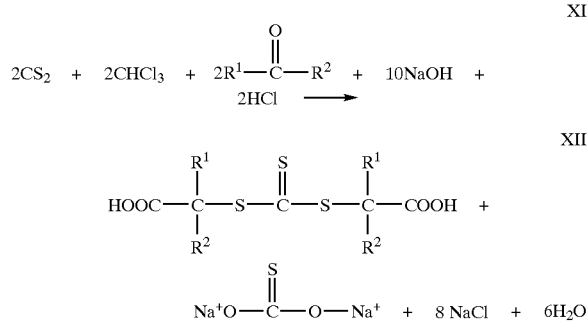

Use of the S,S'-bis-(α,α'—disubstituted—α"—acetic acid)—trithiocarbonate

The s,s'-bis-(α,α'—disubstituted—α"—acetic acid)—trithiocarbonate compounds produced by the present invention can generally be classified as infertors, meaning that they act as both a chain transfer agent and an initiator. The use of other types of inifertors for block copolymers was discussed by Yagei and Schnabel in *Progress in Polymer Science* 15, 551 (1990) and is hereby fully incorporated by reference.

Thus, the compounds of the present invention can be utilized as initiators to initiate or start the polymerization of a monomer. They can also act as a chain transfer agent, which interrupts and terminates the growth of a polymer chain by formation of a new radical which can act as a nucleus for forming a new polymer chain. The compounds can also be utilized as terminators in that when most of initiating radicals and monomers are consumed, the compounds are incorporated in the polymers as a dormant species. Desirably though, another compound, such as those listed herein below, is often used as an initiator in the free radical polymerization process as described herein below, and the s,s'-bis-(α,α'—disubstituted—α"—acetic acid)—trithiocarbonate compounds of the present invention will act as a chain-transfer agent.

The s,s'-bis-(α,α'—disubstituted—α"—acetic acid)—trithiocarbonate compounds of the present invention can also be used as chain transfer agents in a free radical polymerization process to provide polymerizations which have living characteristics and polymers of controlled molecular weight and low polydispersity, as well as for forming telechelic polymers.

A living polymerization is a chain polymerization which proceeds in the absence of termination and chain transfer. The following experimental criteria can be utilized to diagnose a living polymerization.

1. Polymerization proceeds until all monomer has been consumed.

Further addition of monomer results in continued polymerization.

2. The number average molecular weight, $M_n$ (or $X_n$, the number average degree of polymerization), is a linear function of conversion.
3. The number of polymer molecules (and active centres) is constant and independent of conversion.
4. The molecular weight can be controlled by the stoichiometry of the reaction.
5. Narrow molecular weight distribution polymers are produced.
6. Chain-end functionalized polymers can be prepared in quantitative yields.
7. In radical polymerization, the number of active end groups should be 2, one for each end.

Besides those mentioned above, other criteria can also help to determine the living character of polymerization. For radical living polymerization, one is the ability of the polymer isolated from the first step of polymerization to be used as a macroinitiator for the second step of a polymerization in which block copolymers or grafted polymers are ultimately formed. To confirm the formation of block copolymers, measurements of molecular weights and a determination of the structure of the blocks are employed. For structure measurements, the examination of NMR or IR signals for the segments where individual blocks are linked together and a determination of the end groups are both very important. In radical polymerization, only some of the criteria for living polymerizations are actually fulfilled. Due to their ability to undergo further polymerization, these types of polymers can also be called 'reactive polymers'. A more detailed description of living polymerization can be found in "Living Free-Radical Block Copolymerization Using Thio-Inifertors", by Anton Sebenik, *Progress in Polymer Science*, vol. 23, p. 876, 1998.

The living polymerization processes can be used to produce polymers of narrow molecular weight distribution containing one or more monomers sequences whose length and composition are controlled by the stoichiometry of the reaction and degree of conversion. Homopolymers, random copolymers or block polymers can be produced with a high degree of control and with low polydispersity. Low polydispersity polymers are those with polydispersities that are significantly less than those produced by conventional free radical polymerization. In conventional free radical polymerization, polydispersities (polydispersity is defined as the ratio of the weight average to the number average molecular weight $M_w/M_n$) of the polymers formed are typically greater than 2.0. Polydispersities obtained by utilizing the s,s'-bis-(α,α'—disubstituted—α"—acetic acid)—trithiocarbonate compounds and derivatives thereof of the present invention are preferably 1.75 or 1.5, or less, often 1.3 or less, and, with appropriate choice of the chain transfer agent and the reaction conditions, can be 1.25 or less.

When the s,s'-bis-(α,α'—disubstituted—α"—acetic acid)—trithiocarbonates compounds are utilized only as chain-transfer agents, the polymerization can be initiated with other initiators at lower temperature while yielding polymers with similarly controlled fashion.

Free radical polymerizations utilizing the s,s'-bis-(α,α'—disubstituted—α"—acetic acid)—trithiocarbonate compounds as both initiators and chain transfer agents generally form telechelic polymers. When an initiator other than the s,s'-bis-(α,α'—disubstituted—α"—acetic acid)—trithiocarbonate compound is also utilized, a polymer having a single functional end group is formed in proportion to the amount of said other initiator to this s,s'-bis-(α,α'—disubstituted—α"—acetic acid)—trithiocarbonate compound utilized.

The free radical living polymerization process of the invention can be applied to any monomers or monomer combinations which can be free-radically polymerized. Such monomers include one or more conjugated diene monomers or one or more and vinyl containing monomers such as acrylate or methacrylate esters, or combinations thereof.

The diene monomers have a total of from 4 to 12 carbon atoms and examples include, but are not limited to, 1,3-butadine, isoprene, 1,3-pentadiene, 2,3-dimethyl-1-3-butadeine, 2-methyl-1,3-pentadiene, 2,3-dimethyl-1,3-pentadiene, 2-phenyl-1,3-butadiene, and 4,5-diethyl-1,3-octadiene, and combinations thereof.

The vinyl containing monomers have the following structure:

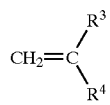

where $R^3$ comprises hydrogen, halogen, $C_1$ to $C_4$ alkyl, or substituted $C_1$–$C_4$ alkyl wherein the substituents, independently, comprise one or more hydroxy, alkoxy, aryloxy($OR^5$), carboxy, acyloxy, aroyloxy($O_2CR^5$) alkoxy-carbonyl($CO_2R^5$), or aryloxy-carbonyl; and $R^4$ comprises hydrogen, $R^5$, $CO_2H$, $CO_2R^5$, $COR^5$, CN, $CONH_2$, $CONHR^5$, $O_2CR^5$, $OR^5$, or halogen. $R^5$ comprises $C_1$ to $C_{18}$ alkyl, substituted $C_1$–$C_{18}$ alkyl, $C_2$–$C_{18}$ alkenyl, aryl, heterocyclyl, aralkyl, or alkaryl, wherein the substituents independently comprise one or more epoxy, hydroxy, alkoxy, acyl, acyloxy, carboxy, (and salts), sulfonic acid (and salts), alkoxy, or aryloxy-carbonyl sicyanato, cyano, silyl, halo and dialkylamino. Optionally, the monomers comprise maleic anhyciride, N-alkylmaleimide, N-arylmaleimide, dialkyl fumarate and cyclopolymerizable monomers. Monomers $CH_2=CR^3R^4$ as used herein include C1–$C_8$ acrylates and methacrylates, acrylate and methacrylate esters, acrylic and methacrylic acid, styrene, α methyl styrene, $C_1$–$C_{12}$ alkyl styrenes with substitute groups both either on the chain or on the ring, acrylamide, methacrylamide, and methacrylonitrile, mixtures of these monomers, and mixtures of these monomers with other monomers. As one skilled in the art would recognize, the choice of comonomers is determined by their steric and electronic properties. The factors which determine copolymerizability of various monomers are well documented in the art. For example, see: Greenley, R. Z., in *Polymer Handbook*, 3$^{rd}$ Edition (Brandup, J., and Immergut, E. H. Eds.) Wiley: New York, 1989 pII/53.

Specific monomers or comonomers include the following: methyl methacrylate, ethyl methacrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, alpha-methylstyrene. methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile. styrene, functional methacrylates, acrylates and styrenes selected from glycidyl methacrylate, 2-hydroxyethyl, methacryliate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, itaconic anhydride, itaconic acid, glycidyl acrylate, 2-hydroxyethyl acrylate, hydroxypropyl acrviate (all isomers), hydroxybutyl acrylate (all isomers), N,N-dimethylaminoethyl acrylate, N,N-diethylaminoethyl acrylate, triethyleneglycol acrylate, methacrylamide, N-methylacrylamide, N,N-dimethylacrylamide, N-terbtbutylmethacrylamide, N-n-butylmethacrylamide, N-methylolmethacrylamide, N-ethylotmethacrylamide. N-tert-butylacrylamide. N-n-butylacrylamide, N-methylolacrylamide, N-ethylolacrylamide, vinyl benzoic acid (all isomers), dethylaminostyrene (all isomers), alpha-methylvinyl benzoic acid (all isomers), dethylamino alpha-methylstyrene (all isomers). p-vinylbenzene sulfonic acid, p-vinylbenzene sulfonic sodium salt, trimethoxysilylpropyl methacrylate, triethoxysilylpropyl methacrylate, tributoxysilyipropyl methacrylate, dimethoxymethylsilylpropyl methacrylate, diethoxymethylslylpropyl methacrylate, dibutoxymethylsilypropyl methacrylate, diisopropoxymethylsilylpropyl methacrylate, dimethoxysilylpropyl methacrylate, diethoxysilylpropyl methacrylate, dibutoxy, silylpropyl methacrylate, diisopropoxysilylpropyl methacrylate, trimethoxysilylpropyl acrylate, triethoxysifylylpropyl acrylate, tributoxysilylpropyl acrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl amiate, vinyl acetate, vinyl butyrate, vinyl benzoate, vinyl chloride, vinyl fluoride, vinyl bromide, maleic anhydride, N-phenylmaleimide, N-butylmaleimide, N-vinylpyrrolidone, N-vinylcarbazole, butadiene, isoprene, chloroprene, ethylene, and propylene, and combinations thereof.

Preferred monomers are $C_1$–$C_{18}$ acrylates, $C_1$–$C_{18}$ methacrylates, vinyl substituted aromatics containing a total of from 8 to about 12 carbon atoms such as styrene, conjugated dienes containing from 4 to about 12 carbon atoms such as butadiene, or isoprene; as well as acrylonitrile. Considering the methacrylates and more desirably the acrylates, the ester portion is an aliphatic, aromatic, or combination thereof containing from 1 to about 18 carbon atoms, desirably as an alkyl containing from 1 to about 8 carbon atoms with 2 to about 4 carbon atoms such as ethyl or butyl being especially preferred for forming carboxyl terminated polyacrylates for subsequent use as a toughener for epoxy resins. The same will be more fully discussed herein below.

As noted above, in order to initiate the free radical polymerization process, it is often desirable to utilize an initiator as a source for initiating free radicals. Generally, the source of initiating radicals can be any suitable method of generating free radicals such as the thermally induced homolytic scission of a suitable compound(s) (thermal initiators such as peroxides, peroxyesters, or azo compounds), the spontaneous generation from monomer (e.g., styrene), redox initiating systems, photochemical initiating systems or high energy radiation such as electron beam, X- or gamma-radiation. The initiating system is chosen such that under the reaction conditions there is no substantial adverse interaction of the initiator or the initiating radicals with the transfer agent under the conditions of the experiment. The initiator should also have the requisite solubility in the reaction medium or monomer mixture. The s,s'-bis-($\alpha,\alpha'$—disubstituted—$\alpha''$—acetic acid)—trithiocarbonate compounds of the invention can serve as an initiator, but the reaction must be run at a higher temperature. Therefore, optionally it is desirable to utilize an initiator other than the s,s'-bis-($\alpha,\alpha'$—disubstituted—$\alpha''$—acetic acid)—trithiocarbonates compounds of the present invention.

Thermal initiators are chosen to have an appropriate half-life at the temperature of polymerization. These initiators can include one or more of the following compounds: 2,2'-azobis(isobutyronitrile)(AIBN), 2,2'-azobis(2-cyano-2-butane), dimethyl 2,2'-azobisdimethylisobutyrate, 4,4'-azobis(4-cyanopentanoic acid), 1,1'-azobis(cyclohexanecarbanitrile), 2-(t-butylazo)-2-cyanopropane, 2,2'-azobis[2-methyl-N-(1,1)-bis(hydoxymethyl)-2-hydroxyethyl]propionamide, 2,2'-azobis[2-methyl-N-hydroxyethyl)]-propionamide, 2,2'-azobis(N,N'-dimethyleneisobutyramidine) dihydrochloride, 2,2'-azobis(2-amidinopropane)dihydrochloride, 2,2'-azobis(N,N'-dimethyleneisobutyramine), 2,2'-azobis(2-methyl-N-[1,1-bis(hydroxymethyl)-2-hydroxyethyl]propionamide), 2,2'-azobis(2-methyl-N-[1,1-bis(hydroxymethyl)ethyl]propionamide), 2,2'-azobis[2-methyl-N-(2-hydroxyethyl) propionamide], 2,2'-azobis(isobutyramide)dehydrate, 2,2'-azobis(2,2,4-trimethylpentane), 2,2'-azobis(2-methylpropane), t-butyl peroxyacetate, t-butyl peroxybenzoate, t-butyl peroxyoctoate, t-butylperoxyneodecanoate, t-butylperoxy isobutyrate, t-amyl peroxypivalate, t-butyl peroxypivalate, di-isopropyl peroxydicarbonate, dicyclohexyl peroxydicarbonate, dicumyl peroxide, dibenzoyl peroxide, dilauroylperoxide, potassium peroxydisulfate, ammonium peroxydisulfate, di-t-butyl hyponitrite, dicumyl hyponitrite.

Another difunctional initiator is a bis-azocyano acid having the formula

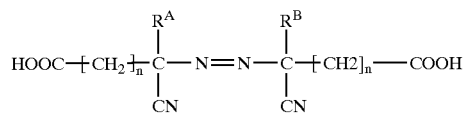

wherein $R^A$ and $R^B$, independently, is an alkyl group of 1–3 carbon atoms, and n, independently, is an integer from 0 to 6. The preferred acids include azodicyanobutyric acid and azodicyanovaleric acid (ADVA), with ADVA being the most preferred. The preparation of these materials is known and disclosed in U.S. Pat. Nos. 3,285,949 and 2,520,338, which are incorporated herein by reference.

Photochemical initiator systems are chosen to have the requisite solubility in the reaction medium or monomer mixture and have an appropriate quantum yield for radical production under the conditions of the polymerization. Examples include benzoin derivatives, benzophenone, acyl phosphine oxides, and photo-redox systems production under the conditions of the polymerization; these initiating systems can include combinations of the following oxidants and reductants:

oxidants: potassium peroxydisuffate, hydrogen peroxide, t-butyl hydroperoxide reductants: iron (11), titanium (111), potassium thiosulfite, potassium bisulfite.

Other suitable initiating systems are described in recent texts. See, for example, Moad and Solomon "The Chemistry of Free Radical Polymerization". Pergamon, London. 1995. pp 53–95.

The preferred initiators of the present invention are 2,2'-azobis(isobutyronitrile)(AIBN), or 4,4'-azobis(4-cyanopentanoic acid), or 2,2'-azobis(2-cyano-2-butane), or 1,1'-azobis(cyclohexanecarbanitrile), or azodicyanobutyric acid or azodicyanovaleric acid (ADVA).

The amount of initiators utilized in the polymerization process can vary widely as generally from about 0.001 percent to about 99 percent, and desirably from about 0.01 percent to about 50 or 75 percent based on the total moles of chain transfer agent utilized. Preferably small amounts are utilized from about 0.1 percent to about 5, 10, 15, 20, or 25 mole percent based on the total moles of said s,s'-bis-($\alpha,\alpha'$—disubstituted—$\alpha''$—acetic acid)—trithiocarbonate compounds. In order to form polymers which are predominately telechelic, initiators other than the s,s'-bis-($\alpha,\alpha'$—disubstituted—$\alpha''$—acetic acid)—trithiocarbonate compounds are utilized in lesser amounts, such as from about 0.001 percent to about 5 percent, desirably from about 0.01 percent to about 4.5 percent, and preferably from about 0.1 percent to about 3 percent based on the molar equivalent to the total moles of chain transfer agent utilized.

Optionally, as noted above, solvents may be utilized in the free radical polymerization process. Examples of such solvents include, but are not limited to, $C_6$–$C_{12}$ alkanes, toluene, chlorobenzene, acetone, t-butyl alcohol, and dimethylformamide. The amount of solvent utilized in the present invention polymerization process is generally from about 10 percent to about 500 percent the weight of the monomer, and preferably from about 50 percent to about 200 percent the weight of the monomer utilized in the polymerization.

As stated above, it is preferable to utilize the s,s'-bis-($\alpha,\alpha'$—disubstituted—$\alpha''$—acetic acid)—trithiocarbonate compounds of the invention as chain transfer agents in the free radical polymerization process. The amount of chain transfer agent (CTA) utilized depends on the desired molecular weight of the polymer to be formed and can be calculated as known by one skilled in the art. A formula for calculating the amount of chain transfer agent is as follows:

$$\text{Mn of polymer} = \left(\frac{\text{Weight of monomer} \times \text{molecular weight } CTA}{\text{Weight of } CTA}\right) + \text{molecular weight of } CTA$$

While not wishing to be limited to any particular mechanism, it is believed that the mechanism of the free radical living polymerization process is as follows when using a vinyl monomer:

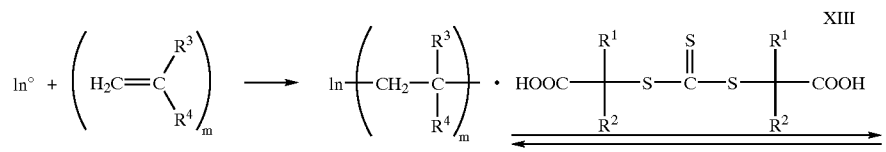
XIII
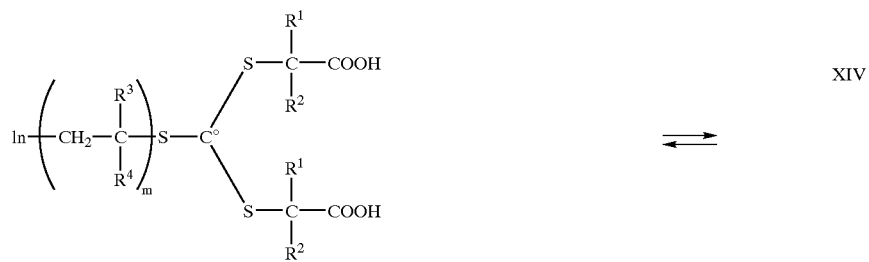
XIV
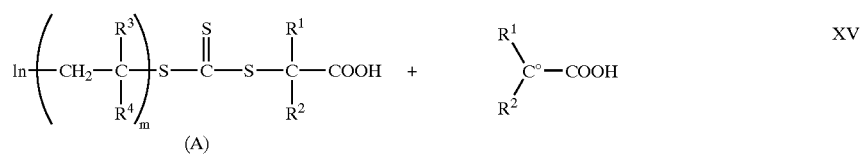
XV
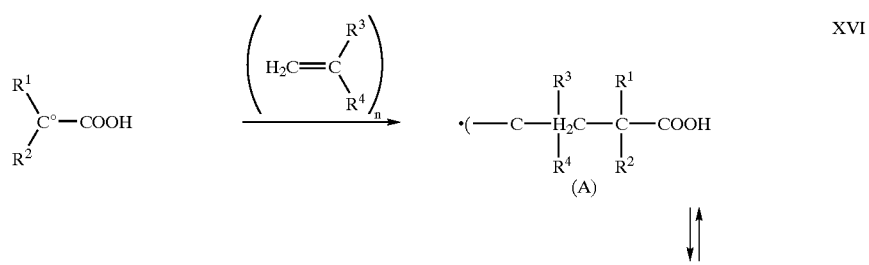
XVI
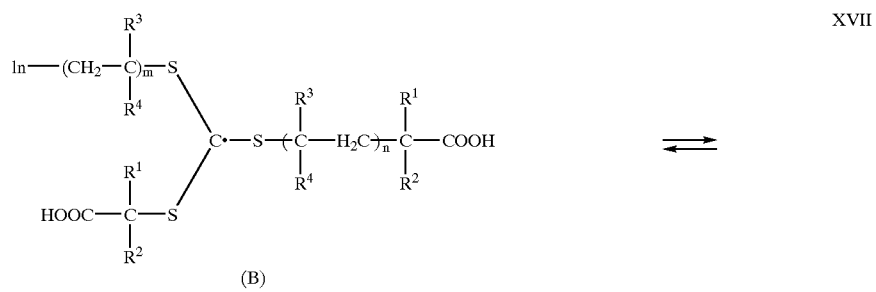
XVII
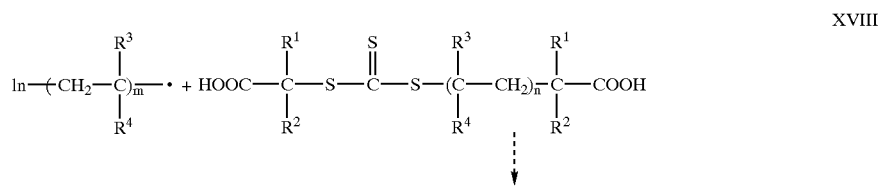
XVIII
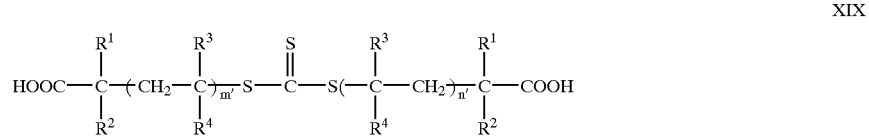
XIX -continued Alternatively, the reaction can proceed as follows:

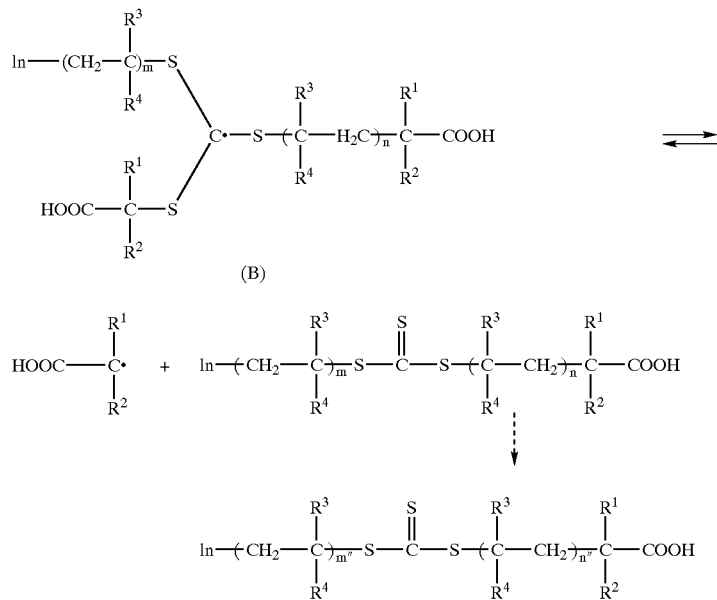

(B)

As can be seen from the above mechanism, polymers having two different structures, see XIX and XXII, can be formed. The resulting polymers are either telechelic polymers (formed by the trithiocarbonate compounds of the present invention) with identical functional groups at the ends of the chain, or a polymer having a single functional end group and also an initiator terminated chain (formed by using a conventional initiator such as AIBN). As stated above, the ratios between the resulting polymers can be controlled to give desired results and generally depends on the amount of initiator utilized. Obviously, if the initiator is the only s,s'-bis-(α,α'—disubstituted—α"—acetic acid)—trithiocarbonate compound of the present invention, the resulting polymers are always telechelic. The greater the amount of the other initiator utilized, proportionally decreases the amount of telechelic polymers formed. Generally, the amount of the repeat group m, m', m", n, n', or n", is generally from about 1 to about 10,000, desirably from about 5 to about 500, and preferably from about 10 to about 200. Inasmuch as one or more vinyl monomers and/or one or more diene monomers can be utilized, it is to be understood that repeat groups of the polymers of the present invention are generally indicated by formulas XIX and XXII and can be the same or different. That is, random copolymers, terpolymers, etc., can be formed within either of the two repeat groups noted, as well as block copolymers which can be formed by initially adding one monomer and then subsequently adding a different monomer (e.g. an internal block copolymer).

Formation of Polymers Using TTC

The polymers formed by the present invention can be generally represented by the following formula:

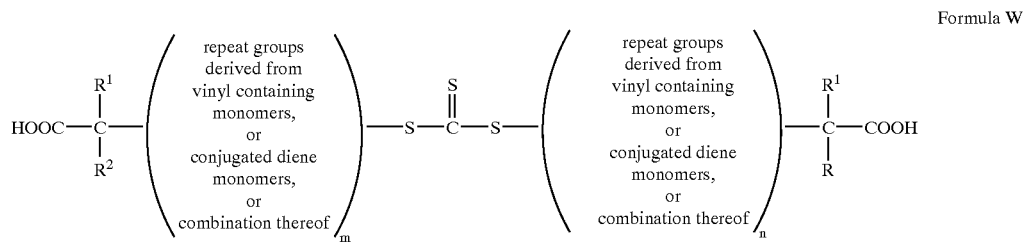

Formula W wherein such monomers are described herein above. Of course, the above formula can contain an initiator end group thereon as in XXII.

The reaction conditions are chosen as known to one skilled in the art so that the temperature utilized will generate a radical in a controlled fashion, wherein the temperature is generally from about room temperature to about 200° C. The reaction can be run at temperatures lower than room temperature, but it is impractical to do so. The temperature often depends on the initiator chosen for the reaction, for example, when AIBN is utilized, the temperature generally is from about 40° C. to about 80° C., when azodicyanovaleric acid (ADVA) is utilized, the temperature generally is from about 50° C. to about 90° C., when di-t-butylperoxide is utilized, the temperature generally is from about 110° C. to about 160° C., when s,s'-bis-(α,α'—disubstituted—α"—acetic acid) is utilized, the temperature is generally from about 80° C. to about 200° C.

The low polydispersity polymers prepared as stated above by the free radical polymerization can contain reactive end groups from the monomers which are able to undergo further chemical transformation or reaction such as being joined with another polymer chain, such as to form block copolymers for example. Therefore, any of the above listed monomers, i.e. conjugated dienes or vinyl containing monomers, can be utilized to form block copolymers utilizing the s,s'-bis-($\alpha,\alpha'$—distributed—$\alpha''$—acetic acid)—trithiocarbonate compounds as chain transfer agent. Alternatively, the substituents may be non-reactive such as alkoxy, alkyl, or aryl. Reactive groups should be chosen such that there is no adverse reaction with the chain transfer agents under the conditions of the experiment.

The process of this invention can be carried out in emulsion, solution or suspension in either a batch, semi-batch, continuous, or feed mode. Otherwise-conventional procedures can be used to produce narrow polydispersity polymers. For lowest polydispersity polymers, the chain transfer agent is added before polymerization is commenced. For example, when carried out in batch mode in solution, the reactor is typically charged with chain transfer agent and monomer or medium plus monomer. The desired amount of initiator is then added to the mixture and the mixture is heated for a time which is dictated by the desired conversion and molecular weight. Polymers with broad, yet controlled, polydispersity or with multimodal molecular weight distribution can be produced by controlled addition of the chain transfer agent over the course of the polymerization process.

In the case of emulsion or suspension polymerization the medium will often be predominately water and the conventional stabilizers, dispersants and other additives can be present. For solution polymerization, the reaction medium can be chosen from a wide range of media to suit the monomer(s) being used.

As already stated, the use of feed polymerization conditions allows the use of chain transfer agents with lower transfer constants and allows the synthesis of block polymers that are not readily achieved using batch polymerization processes. If the polymerization is carried out as a feed system the reaction can be carried out as follows in an inert atmosphere such as nitrogen or argon. The reactor is charged with the chosen medium, the chain transfer agent and optionally a portion of the monomer(s). The remaining monomer(s) is placed into a separate vessel. Initiator is dissolved or suspended in the reaction medium in another separate vessel. The medium in the reactor is heated and stirred while the monomer+medium and initiator+medium are introduced over time, for example by a syringe pump or other pumping device. The rate and duration of feed is determined largely by the quantity of solution the desired monomer/chain transfer agent/initiator ratio and the rate of the polymerization. When the feed is complete, heating can be continued for an additional period.

Following completion of the polymerization, the polymer can be isolated by stripping off the medium and unreacted monomer(s) or by precipitation with a non-solvent. Alternatively, the polymer solution/emulsion can be used as such, if appropriate to its application.

The invention has wide applicability in the field of free radical polymerization and can be used to produce polymers end compositions for coatings, including clear coats and base coat finishes for paints for automobiles and other vehicles or maintenance finished for a wide variety of substrates. Such coatings can further include pigments, durability agents, corrosion and oxidation inhibitors, rheology control agents, metallic flakes and other additives. Block and star, and branched polymers can be used as combatibilizers, thermoplastic elastomers, dispersing agents or rheology control agents. Additional applications for polymers of the invention are in the fields of imaging, electronics (e.g., photoresists), engineering plastics, adhesives, sealants, and polymers in general.

As can be seen in the above shown polymerization mechanism, the s,s'-bis-($\alpha,\alpha'$—disubstituted—$\alpha''$—acetic acid)—trithiocarbonate compound can be utilized to create telechelic polymers.

The term "telechelic polymer" was proposed in 1960 by Uraneck et al. to designate relatively low molecular weight macromolecules possessing one or more, and preferably two reactive functional groups, situated at the chain ends, thereof. The functional end groups of both the s,s'-bis-($\alpha,\alpha'$—disubstituted—$\alpha''$—acetic acid)—trithiocarbonate compound and the polymers formed therefrom, have the capacity for selective reaction to form bonds with another molecule. The functionality of a telechelic polymer or prepolymer is equal to the number of such end groups. Telechelic polymers containing a functional group, such as COOH, at each end are useful for synthesizing further chain extended copolymers and block copolymers.

The interest in telechelic polymers resides in the fact that such polymers can be used, generally together with suitable linking agents, to carry out three important operations: (1) chain extension of short chains to long ones by means of bifunctional linking agents, (2) formation of networks by use of multifunctional linking agents, and (3) formation of (poly)block copolymers by combination of telechelics with different backbones. These concepts are of great industrial importance since they form the basis of the so-called "liquid polymer" technology exemplified by the "reaction injection molding" (RIM). Great interest has also been shown by the rubber industry because the formation of a rubber is based on network formation. In classical rubber technology, this is achieved by the cross-linking of long chains that show high viscosity. The classical rubber technology, therefore, requires an energy-intensive mixing operation. The use of liquid precursors, which can be end-linked to the desired network, offers not only processing advantages, but in some cases, also better properties of the end-product. Further information about telechelic polymers and synthesis thereof can be found in "Telechelic Polymers: Synthesis and Applications" by Eric J. Goethe, CRC Press, Boca Raton, Fla., 1989.

The reaction conditions for the reactive functional acid end groups of the telechelic polymers or s,s'-bis-($\alpha,\alpha'$—disubstituted—$\alpha''$—acetic acid)—trithiocarbonate compounds of the present invention are generally the same as those for forming the above noted free radical polymers. The acid in the monomeric or in the polymeric form can be transformed to its derivatives in the conventional manner. For example, the ester can be made by refluxing the acid in alcohol with an acid catalyst with removal of water. Amides can be formed by heating the acid with an amine with the removal of water. 2-hydroxy-ethyl ester can be formed by directly reacting the acid with an epoxide with or without a catalyst such as triphenylphosphine or an acid like toluenesulfonic acid. As seen by the examples below, any of the above noted monomers such as the one or more diene monomers or one or more vinyl containing monomers, can be utilized to form the telechelic monomers from the bis-($\alpha,\alpha'$—distributed—$\alpha''$—acetic acid)—trithiocarbonate compounds of the present invention. Any of the above noted components, such as solvent, etc., can be utilized in the herein above stated amounts.

The acid groups of the s,s'-bis-($\alpha,\alpha'$—disubstituted—$\alpha''$—acetic acid)—trithiocarbonate compound can be converted to other functional groups either before or after polymerization. Even if the s,s'-bis-(α,α'—disubstituted—α"—acetic acid)—trithiocarbonate compounds have functional end groups which have been converted from the acid end groups before polymerization, the monomers added during polymerization still add to the chain between the sulfur-tertiary carbon as shown in the mechanisms above as well as below at XXIII and XXIV. The carboxylic end groups of the s,s'-bis-(α,α'—disubstituted—α"—acetic acid)—trithiocarbonate compounds or the polymerized s,s'-bis-(α,α'—disubstituted—α"—acetic acid)—trithiocarbonate compounds can be converted or changed into other functional end groups such as esters, thioesters, amides, beta mercapto esters, beta hydroxy esters, or beta amino esters. Examples of these functional end groups are shown below.

An example reaction forming a telechelic polymer from the s,s'-bis-(α,α'—disubstituted—α"—acetic acid)—trithiocarbonate compounds of the invention when using a vinyl monomer as noted above, is as follows:

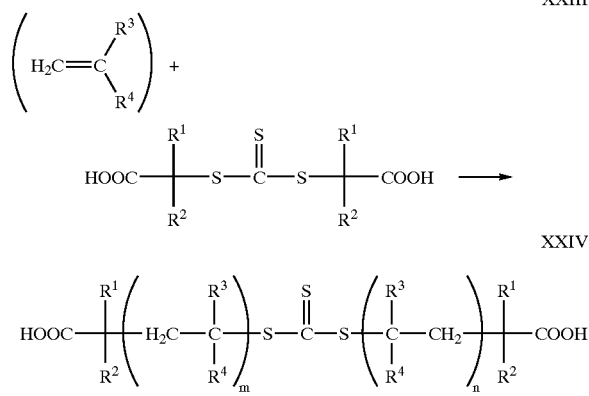

XXIII

XXIV

Of course, it is to be understood as indicated above, that the repeat units m and n can be derived either from conjugated diene monomers, or the indicated vinyl monomers, or combinations thereof, as generally set forth in formula W.

Subsequently, other functional end groups can be derived from the acid groups of the s,s'-bis-(α,α'—disubstituted—α"—acetic acid)—trithiocarbonate compound and can generally be represented by the formula:

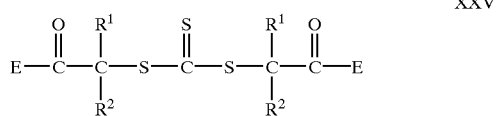

XXV where E is set forth below. For example,

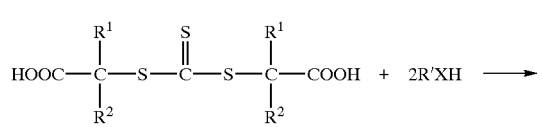

XXVI

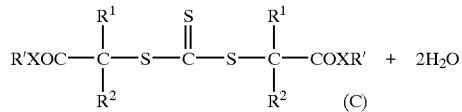

XXVII wherein E is XR', that is R', independently, comprises H, $C_1$–$C_{18}$ alkyls which can be optionally substituted with one or more halogen, hydroxyl, or alkoxy, $C_1$–$C_{18}$ hydroxyalkyls, and $C_1$–$C_{18}$ aminoalkyls and X comprises oxygen, sulfur, NH, or NR'.

The following is still another example of functional end groups which can be derived from the acid:

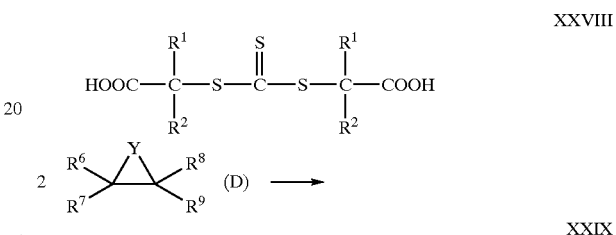

XXVIII

XXIX wherein E is

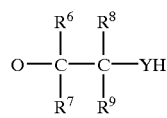

XXX that is, where $R^6$ through $R^9$, independently comprise H, $C_1$–$C_{18}$ alkyls, aryl groups or substituted aryl groups having from 1 to 6 substituents on the ring, such as halogen, hydroxyl, or alkoxy, $C_1$–$C_{18}$ hydroxyalkys, $C_1$–$C_{18}$ aminoalkyls, $C_1$–$C_{18}$ mercapto alkyls, and the like. Y can comprise oxygen, sulfur, NH, or $NR^6$ to $R^9$.

A further example of still other functional end groups which can be derived from the acid groups of the s,s'-bis-(α,α'—disubstituted—α"—acetic acid)—trithiocarbonate compounds is as follows:

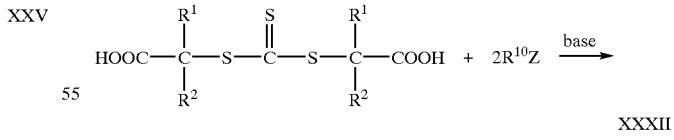

XXXI

XXXII

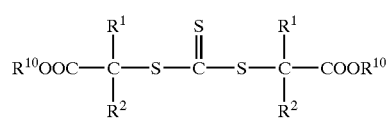

wherein E is $OR^{10}$, that is where Z can comprise a leaving group, such as a halide or alkylsulfonate or aryl sulfonate. $R^{10}$ can comprise $C_1$–$C_{18}$, a alkyl or substituted alkyl wherein said substituent is halogen, hydroxyl, or alkoxy, $C_1$–$C_{18}$ hydroxyalkyl or $C_1$–$C_{18}$ amino alkyl and the like.

Preparation of the above shown methylesters of s,s'-bis-(2-methyl-2-propanoic acid)-trithiocarbonate is as follows: s,s'-bis-(2-methyl-2-propanoic acid) trithiocarbonate ($R^1$, $R^2$=$CH^3$) (2.82 g, 0.01 mole), Sodium carbonate powders (3.18 g, 0.03 mole) and 15 ml dimethyl formamide were stirred under nitrogen at 40° C. while a solution of methyliodide (3.41 g, 0.024 mole) in 2 ml dimethylformamide was added dropwise over 10 minutes. The reaction was stirred at 40–50° C. for 2 hours, poured into 25 ml $H_2O$ and extracted 3 times with a total of 200 ml. ether. The etherate solution was dried over magnesium sulfate and concentrated. The yellow solid was further purified by recrystallization from hexanes. Infrared and H'NMR showed the above desired product.

An example of an already formed telechelic polymer, made fram a vinyl monomer, undergoing conversion of the acid end group, is as follows:

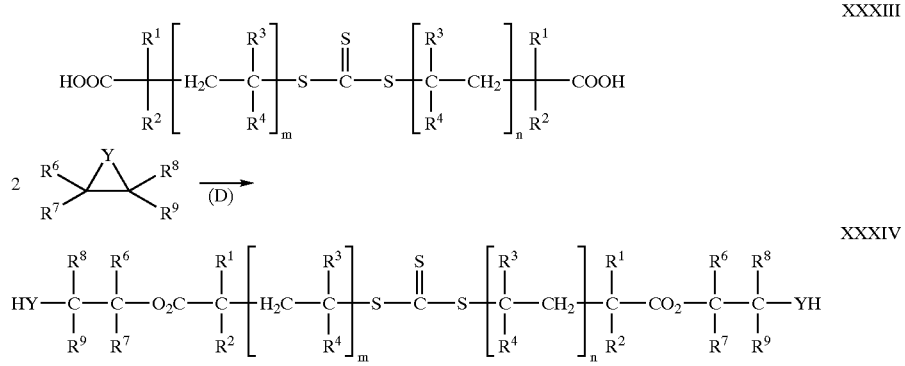

where m and n are as set forth above.

The above structure (XXXIV) was formed by reaction of epoxide with s,s'-bis-(2-methyl-2-propanoic acid)—trithiocarbonate (I)($R^1$,$R^2$=$CH_3$, 0.01 mole) of the present invention and Epon® Resin 828 now owned by (Resolution Performance Products, reaction product of bisphenol A and epichlorohydrin, 80–85% diglycidyl ethers of bisphenol A) (70 g) and triphenyl phosphine (0.12 g) were heated to 95° C. under nitrogen. The reaction was monitored for the disappearance of the carboxylic acid by titration. It was found the reaction was essentially complete in 1.5 hours. The product structure can be further confirmed by mass spectroscopy. This aspect of the invention will be discussed in further detail herein below, especially with regard to toughened epoxy resins.

Another aspect of present invention further relates to forming the following compounds:

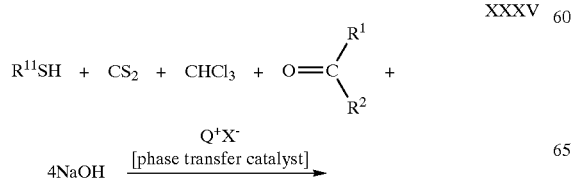

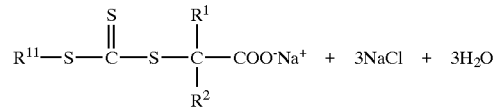

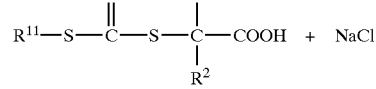

wherein $R^{11}$ comprises a benzyl group, $C_1$–$C_{18}$ alkyl, or substituted alkyl such as halogen, hydroxyl, or alkoxy, $C_1$–$C_{18}$ hydroxyalkyl, carboxylalkyl, or carboalkoxyalkyl. $Q^+$ $X^-$ is a phase transfer catalyst such as tetrabutylammoniumhydrogensulfate, or octadecyltrimethylammoniumchloride (Aliquot 336).

The resulting compound is an s-substituted alkyl—s'-(α, α'—disubstituted—α"—acetic acid)—trithiocarbonate. $R^{11}$ is an alkyl having from 1–18 carbon atoms, aralkyl, hydroxyalkyl, cyanoalkyl, aminoalkyl, carboxylalkyl, or carboalkoxyalkyl, mercaptoalkyl, etc. $R^1$ and $R^2$ are as stated herein above.

When s—substituted alkyl—s'-(α,α'—disubstituted—α"—acetic acid)—trithiocarbonate is employed either as an inifertor, or as a chain-transfer agent, unless $R^{11}$ is carboxyl alkyl, only one end of the polymer has a carboxyl function, i.e. it is no longer a telechelic polymer.

While various polymers have been set forth herein above, it is to be understood that any of the carboxyl terminated polymers, such as W, or the E terminated polymers, and the like, can be reacted with one or more monomers and/or one or more polymers know to the art and to the literature to yield various resulting block polymers which are derived from the same monomer or from two or more different monomers. For example, each acid end group can be reacted with an excess of an epoxy compound such as a glycidyl bisphenol A and then subsequently polymerized with additional glycidyl bisphenol A to form an epoxy polymer. Naturally, other block polymers or copolymers can be reacted with the carboxylic end group or the other end groups generally denoted by E herein above.

Toughened Thermoset Resins

The trithiocarbonate polymers are generally set forth in Formulas W and XXIV and can be made according to any of the methods set forth hereinabove and is hereby fully incorporated by reference where $R^1$ and $R^2$ are as indicated and preferably are methyl. Such polymers containing carboxyl end groups, or when modified as set forth herein below to have epoxy end groups, serve as effective tougheners for various thermoset compounds or polymers such as epoxy resins, polyurethanes, polyesters, polyacrylates, epoxy (meth)acrylates, polyvinyl esters, or cyanate esters, and the like.

The preparation of carboxyl terminated polymers generally involves reacting the trithiocarbonates with suitable monomers such as alkyl acrylates, using free radical initiators. The reaction can be a bulk polymerization, or preferably in the presence of a monomer or oligomer which not only can serve as a solvent, but later reacted with the formed polymer. As noted above, suitable acrylic or methacrylic monomers include alkyl alkacrylates wherein the alkyl is from 1 to about 18 carbon atoms and the alk group has from 1 to about 3 carbon atoms such as methyl methacrylate or more preferably an alkyl acrylate wherein the alkyl portion has from 1 to about 8 carbon atoms with ethylacrylate, butylacrylate and ethyl-hexyl acrylate being highly preferred. The one or more acrylate monomers is incorporated into the backbone of the polymer adjacent to the trithiol group as shown in Formulas W and XXIV. Thus, the acrylate monomers will react and form acrylate repeat units on either side of the trithio group of the trithio carboxylate. The number of repeat units, that is "m" and "n" of the acrylate units, independently, is generally from about 5 to about 500 or about 1,000, desirably from about 7 to about 150, and preferably from about 10 to about 20, 30, 50 or 200.

Of course, in lieu of the acrylate acrylic monomers, other monomers noted hereinabove can be used such as vinyl substituted aromatics having from 8 to 12 carbon atoms, conjugated dienes having from 4 to 12 carbon atoms, acrylonitrile, and the like.

The reaction conditions for forming the carboxyl terminated polymers of Formula W and XXIV are generally the same as set forth herein above. That is, a desired polymerization temperature is from about 25° C. to about 200° C., and will vary with the initiator. Desirable polymerization temperatures range from about 40° C. to about 125° C. with from about 50° C. to about 90° C. being preferred as in Examples 5 and 6. The initiators can be various peroxides or azo compounds as set forth hereinabove with AIBN and ADVA being highly preferred. While trithiocarbonate (TTC) can also be utilized as an initiator, it is not preferred. The amount of the initiator is generally small and can range from about 0.001 to about 20 and desirably from about 0.002 to about 5 parts by weight for every 100 parts by weight of the acrylate, or other monomers. With respect to the solvent, while it can be the same as set forth hereinabove, desirably it is an epoxy resin such as the reaction product of Bisphenol A and epichlorohydrin which is commercially available as Epon 828 from Resolution Performance Products as set forth herein below. A liquid epoxy resin is desirably utilized as a solvent since it will not react with the noted initiators such as AIBN or ADVA but will react in a subsequent step. A preferred form of a carboxyl terminated polymer containing acrylate repeat groups which also acts as a toughener for thermosettable polymers, is set forth in Formula Y.

Formula Y

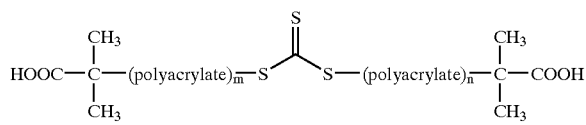

where m and n are as set forth above.

The number average molecular weight of each (polyacrylate), independently, is generally from about 1,000 to about 50,000 with from about 5,000 to about 20,000 being preferred.

In lieu of the (polyacrylate) in Formula Y, polymers derived from conjugated diene monomers, vinyl substituted aromatic monomers, or acrylonitrile can exist.

In order to form a thermoset toughener such as an epoxy toughener, it is desirable to add epoxy end groups to the carboxyl terminated polyacrylate of Formula Y in a manner as shown in Formulas XXXIII and XXXIV. While the following relates the addition of epoxy end groups to a polyacrylate as set forth in Formula Y, it is to be understood that similar reaction conditions exists for polymers containing repeat groups derived from vinyl substituted aromatic monomers, from conjugated diene monomers, and from acrylonitrile monomers. Accordingly, these various monomers can be polymerized in the presence of a solvent including an epoxy resin. The addition of a specific catalyst will induce epoxy termination of the acrylate, etc., polymer. Metal salts are generally utilized as catalysts, such as zinc chloride, zinc acetate, and other Lewis acids; or various phosphonium salts such as, tetrabutylphosphonium bromide, or a phosphine such as triphenylphosphine, which is preferred. Reaction temperatures can vary from about 25° C. to about 150° C., desirably from about 50° C. to about 130° C., with from about 80° C. to about 110° C. being preferred. The amount of the various catalysts is generally from about 0.00 1 to about 5 and desirably from about 0.005 to about 1 parts by weight for every 100 parts by weight of said carboxyl-terminated polymers. U.S. Pat. No. 4,530.962 is also hereby fully incorporated by reference with regard to reaction conditions for adding terminal epoxy groups to compounds of Formula Y containing internal polyacrylates, polymerized vinyl substituted aromatics, polymerized conjugated dienes, and the like.

The carboxyl or epoxy terminated polymer toughener is generally deseribed by Formula Z Formula Z

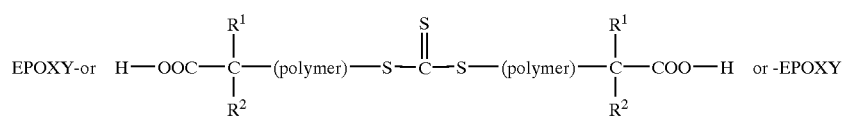

wherein EPOXY is derived from an epoxy resin and generally has from about 1 to about 3 repeats units or less, desirably 3 repeat units or less, preferably about 1 to about 2 units with slightly more than a single repeat unit being highly preferred. That is, a plurality of polymers of Formula Z will exist wherein a majority of the polymer ends are terminated by a single epoxy group with some polymers being terminated with two or three epoxy groups.

The carboxyl groups of carboxyl end-functional polyacrylates may be converted to many other functional groups some of those being, vinyl, epoxy, amine, primary and secondary hydroxyl by reacting the carboxyl groups with glycidyl methacrylate, di-functional epoxies, poly-functional amines and ethylene or mono-functional epoxies.

The epoxy resins which are modified with the toughener or adducts such as those set forth in Formula Y to add epoxy end groups thereto are commercially available and known to the art and to the literature. Desirable epoxy resins include polyhydric phenol polyether alcohols; glycidyl ethers of novolac resins such as epoxylated phenol-formaldehyde novolac resin; glycidyl ethers of mononuclear di- and tri-hydric phenols; glycidyl ethers of bisphenols such as dig-lycidyl ether of tetrabromobisphenol A; glycidyl ethers of polynuclear phenols; epoxy resin from diphenolic acid; glycidyl ethers of aliphatic polyols such as chlorine-containing aliphatic diepoxy and polyepichlorohydrin; glycidyl esters such as aliphatic diacid glycidyl esters and epoxidized phenolphthalein; glycidyl epoxies containing nitrogen such as glycidyl amides and amide-containing epoxies; glycidyl derivatives of cyanuric acid; glycidyl resins from melamines; glycidyl amines such as triglycidyl ether amine of p-aminophenol and bis(2,3-epoxypropyl) methylpropylammonium p-toluenesulfonate; and glycidyl triazines; thioglycidyl resins such as epoxidized bisulfide; silicon-glycidyl resins such as 1,4-bis[(2,3-epoxypropoxy) dimethylsilyl]; fluorine glycidyl resins; epoxy resins which are synthesized from monoepoxies other than epihalohydrins including epoxy resins from unsaturated monoepoxies such as polyallyl glycidyl ether and glycidyl sorbate dimer; epoxy resins from monoepoxy alcohols; epoxy resins from monoepoxies by ester interchange; epoxy resins from glycidaldehyde; polyglycidyl compounds containing unsaturation such as allyl-substituted diglycidyl ether of bisphenol A; epoxy resins which are synthesized from olefins and chloroacetyls such as butadiene dioxide, vinylcyclohexene dioxide, epoxidized polybutadiene, and bis(2,3-epoxycyclopentyl)ether; or epoxy-resin adducts of the above. A more comprehensive list of epoxy resins can be found in Handbook of Epoxy Resins, by Henry Lee and Kris Neville, McGraw-Hill, Inc., 1967, which is hereby incorporated by reference. A highly preferred epoxy resin polymer for use in the present invention is diglycidyl ether of bisphenol A (DGEBA) which has the following structural formula:

Epoxy terminated polymers such as those represented by Formula Z serve as tougheners for thermoset resins such as epoxy resins inasmuch as they are somewhat flexible, that is less brittle than conventional epoxy resins.

As noted above, the toughener, be it carboxyl terminated or epoxy terminated, serves to either toughen or flexiblize various polymers which are subsequently crosslinked to form a thermoset. Such thermosettable polymers include epoxy resins, various polyurethanes, various polyacrylates, various polyvinyl esters, various polyesters, various cyanate esters, or epoxy (meth)acrylates and the like, all known to the art and to the literature. However, epoxy resins are preferred.

Epoxy Resins

Suitable thermosettable epoxy resins which can be utilized are known to the art and to the literature and include the same resins as set forth herein immediately above with respect to end capping the toughener and are hereby fully incorporated by reference for the sake of brevity. A highly preferred epoxy resin is the diglycidyl ether of bisphenol A which is also set forth herein immediately above.

Polyurethanes

Suitable thermosettable polyurethanes are known to the literature and to the art and are generally prepared by reacting a polyisocyanate and optionally one or more chain extenders with an intermediate such as a hydroxyl terminated polyester, a hydroxyl terminated polyether, a hydroxyl terminated polycarbonate (i.e., a polycarbonate polyol), or mixtures thereof.

A preferred class of hydroxyl terminated polyester intermediates is generally a linear polyester having a molecular weight of from about 500 to about 10,000, desirably from about 700 to about 5,000. The polyester intermediates are produced by (I) an esterification reaction of one or more glycols with one or more dicarboxylic acids or anhydrides, or (2) by transesterification reaction, i.e., the reaction of one or more glycols with esters of dicarboxylic acids. Mole ratios generally in excess of more than one mole of glycol to acid are preferred so as to obtain linear chains having a preponderance of terminal hydroxyl groups.

The dicarboxylic acids can be aliphatic, cycloaliphatic, aromatic, or combinations thereof. Suitable dicarboxylic acids which may be used alone or in mixtures usually have a total of from 4 to 20 carbon atoms and include: succinic, glutaric, adipic, pimelic, suberic, azelaic, sebacic, dodecanoic, isophthalic, terephthalic cyclohexane dicarboxylic, and the like. Anhydrides of the above dicarboxylic acids, such as phthalic anhydride, tetrahydrophthalic anhydride, or the like, can also be utilized.

The ester-forming glycols can be aliphatic, aromatic, or combinations thereof; have a total of from 2 to 15 carbon atoms; and include: ethylene glycol, propylene glycol,

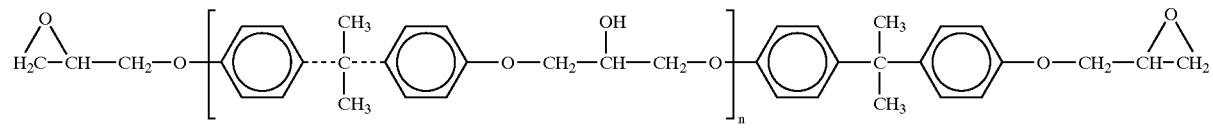

wherein n is an integer from 0 to about 18, desirably from 0 to about 1.5, and preferably from 0 to about 6. The weight average molecular weight of DGEBA is from about 340 to about 4,000, and preferably from about 340 to about 2,600.

butanediol, pentanediol, hexanediol, dimethylpropane diol, cyclohexanedimethanol, decamethylene glycol, dodecamethylene glycol, and the like, with butanediol being a desired glycol.

Suitable polycarbonate polyols can also be utilized as an intermediate, and the same, as well as methods of preparation thereof, are disclosed in U.S. Pat. No. 4,643,949, which is hereby fully incorporated by reference. Other low molecular weight polycarbonate polyol intermediates can also be made from diols such as those set forth hereinabove, including 1,6-hexanediol, and the like, and phosgene; or by transesterification with low molecular weight carbonates such as diethyl or diphenyl carbonate.

The hydroxyl terminated polyethers can be polyether polyols derived from a diol or polyol having a total of from 2 to 15 carbon atoms, preferably an alkyl diol or glycol which is reacted with an ether comprising an alkylene oxide having from 2 to 6 carbon atoms, typically ethylene oxide or propylene oxide, or mixtures thereof. For example, hydroxyl functional polyether can be produced by first reacting propylene glycol with propylene oxide followed by subsequent reaction with ethylene oxide. Primary hydroxyl groups resulting from ethylene oxide are more reactive than secondary hydroxyl groups and thus are preferred. Useful commercial polyether polyols include poly(ethylene glycol), poly(propylene glycol), poly(propylene-ethylene glycol), poly (tetramethylene ether glycol) (PTMEG), copolyethers produced from tetrahydrofuran (THF) and ethylene oxide or THF and propylene oxide, glycerol adduct comprising glycerol reacted with propylene oxide, trimethylolpropane adduct comprising trimethylolpropane reacted with propylene oxide, pentaerythritol adduct comprising pentaerythritol reacted with propylene oxide, and similar hydroxyl functional polyethers.

In addition to the above polyether type intermediates, other intermediates can be utilized known to those skilled in the art as well as to the literature such as those having different molecular weights, made from different reactants, and the like.

The above-mentioned polyols can be used alone or in any combination.

The intermediate, such as a hydroxyl terminated polyester, a polyether, etc., is further reacted with one or more polyisocyanates. The urethane can be made in a conventional two-step process wherein initially a prepolymer is made from the polyisocyanate and the intermediate, with the prepolymer subsequently being reacted with a chain extender glycol. The equivalent ratio of the one or more diisocyanates to the hydroxyl terminated intermediate is generally a sufficient amount such that upon subsequent chain extension with a suitable glycol, the overall equivalent ratio of the hydroxyl terminated compounds to the one or more polyisocyanates is approximately 0.95 to about 1.06, and the like. Often it can be an excess such as up to about 1.20 or less, or 1.15 or less. Suitable polyisocyanates which can be utilized generally have the formula R(NCO)$_n$ wherein n is generally 2, 3, or 4, or fractions thereof if blends are utilized. R is an aliphatic having from 2 to about 20 carbon atoms with from about 6 to about 15 carbon atoms being preferred, or an aromatic including an alkyl substituted aromatic having from about 6 to about 20 carbon atoms with from about 6 to about 15 carbon atoms being preferred, or combinations thereof. Suitable diisocyanates include non-hindered aromatic diisocyanates such as: 4,4'-methylenebis-(phenyl isocyanate) (MDI); isophorone diisocyanate (IPDI), m-xylene diisocyanate (XDI), as well as non-hindered cyclic aliphatic diisocyanates such as 1,4-cyclohexyl diisocyanate (CHDI), decane-1,10-diisocyanate, phenylene-1,4-diisocyanate, naphthylene-1,5-diisocyanate, diphenylmethane-3,3'-dimethoxy-4,4'-diisocyanate, dicyclohexylmethane-4,4'-diisocyanate, and cyclohexyl-1, 4-diisocyanate, hexane diisocyanate (HDI), toluene diisocyante (TDI), as well as combinations thereof. The preferred diisocyanate is 4,4'-methylenebis(phenyl isocyanate) i.e., MDI.

Suitable extender glycols (i.e., chain extenders) are saturated low molecular weight glycols, preferably aliphatic, and in particular, alkylene glycols containing from 2 to about 12 carbon atoms. These normally have molecular weights not over about 300. Representative glycols include ethylene glycol, diethylene glycol, propylene glycol, dipropylene glycol, 1,4-butanediol, 1,6-hexanediol, 1,3-butanediol, 1,5-pentanediol, 1,4-cyclohexane-dimethanol, hydroquinone di(hydroxyethyl)ether, diethylene glycol, neopentyl glycol and 3-methyl-1,5-pentanediol, as well as cycloaliphatic and aromatic glycols, and combinations thereof, with 1,4-butanediol being preferred.

The reaction is generally initiated at temperatures above 100° C. and desirably above 120° C. Inasmuch as the reaction is exothermic, the reaction temperature generally increases to about 200° C. to 280° C.

Examples of the above, as well as other suitable polyurethanes which can be utilized, are set forth in Vol. 13 of the Encyclopedia of Polymer Science and Engineering, John Wiley & Sons, Inc., New York, N.Y., 1988, pages 243–303, which is hereby fully incorporated by reference.

Conventional urethane catalysts are generally utilized known to the art and to the literature and generally include various tin compounds such as stannous carboxylates, for example stannous acetate, stannous octoate, stannous laurate, stannous oleate and the like; or dialkyl tin salts of carboxylic acids such as dibutyltin diacetate, dibutyltin dilaurate, dibutyltin maleate, dibutyltin di-2-ethylhexoate, dilauryltin diacetate, dioctyltin diacetate and the like. Similarly, there can be used a trialkyltin hydroxide, dialkyltin oxide or dialkyltin chloride. As an alternative or in addition to the above tin compounds. The tin catalysts, when utilized, are generally used in amounts of 1.0 or 0.5 parts or less, i.e., in the range of about 0.01 to 0.5 parts, by weight per 100 parts of prepolymer.

Thermosetting polyurethanes are made by utilizing either polyisocyanates having more than 2 reactive isocyanate groups and/or chain extenders which have more than 2 reactive sites as noted herein above.

Polyacrylates

Suitable thermosettable polyacrylates are known to the art and to the literature and are generally made from acrylate monomers having the formula

wherein $R^1$ is an aliphatic (especially an alkyl), having from 1 to 3 carbon atoms, or a halogen derivative thereof, desirably is methyl or hydrogen, and preferably is hydrogen. $R^2$ is hydrogen or an aliphatic group, especially an alkyl, an aromatic, an alkyl hydroxyl, or combinations thereof, having from 1 to 18 carbon atoms, desirably from 2 to 10 carbon atoms, and preferably from 2 to 8 carbon atoms, or a halogen derivative thereof; or $R^2$ is a hydrocarbyl ether such as alkoxyalkyl, a phenoxyaryl, or a phenoxyalkyl, or combinations thereof having from 2 to 1,000 carbon atoms, desirably from 2 to 18 carbon atoms, and preferably from 2 to 8 carbon atoms, or a substituted halogen, oxygen, nitrogen, or sulfur derivative thereof. Examples of specific acrylate monomers include ethyl acrylate, propyl acrylate, butyl acrylate, hexyl acrylate, octyl acrylate, 2-ethylhexyl acrylate, nonyl acrylate, decyl acrylate, phenyl acrylate, nonylphenyl acrylate, ethyl methacrylate, butyl methacrylate, hexyl methacrylate, 2-ethylhexyl methacrylate, methoxymethyl acrylate, methoxyethyl acrylate, ethoxyethyl acrylate, butoxyethyl acrylate, ethoxypropyl acrylate, 2(2-ethoxyethoxy)ethyl acrylate, and the like. Especially preferred acrylate monomers include butyl acrylate, 2-ethylhexyl acrylate, ethyl acrylate, and the like. As noted hereinabove, the $R^2$ group can be a hydrocarbyl ether group. That is, it can be an ether, a diether, or a multiple ether of an alkyl, an aryl, or combinations thereof, such as an alkoxyalkyl, a phenoxyaryl, a phenoxyalkyl, and the like, generally having from 2 to 1,000 carbon atoms, desirably from 2 to 18 carbon atoms, and preferably from 2 to 8 carbon atoms, or combinations thereof. Examples of specific alkoxyalkyl acrylates include methoxymethyl acrylate, butoxyethyl acrylate; ethoxypropyl acrylate, methoxyethyl acrylate, ethoxyethyl acrylate, 2(2-ethoxyethoxy) ethylacrylate, and the like. Examples of specific phenoxyalkyl acrylates include 2-phenoxylethylacrylate and 2-phenoxyethylmethacrylate. In addition to the above $R^2$ ether groups, halogen, oxygen, nitrogen, or sulfur derivatives of such hydrocarbyl ether groups can also be utilized. For example, $R^2$ can be an alkoxyalkyl containing at least one halogen therein in lieu of a hydrogen atom.

The polyacrylates are crosslinked by a number of mechanisms known to the art and to the literature. For example, urethane modified olefinic-terminated liquid elastomers can be utilized to crosslink the various polyacrylates as set forth in U.S. Pat. No. 4,769,419, hereby fully incorporated by reference.

Polyesters

Suitable thermosettable polyesters are known to art and to the literature and are generally made by a condensation polymerization reaction generally between at least one polycarboxylic acid or an anhydride thereof and a polyol. Reaction temperatures will vary depending upon the monomers, catalyst, and the like and generally range from about 100 to about 300° C. A polycarboxylic acid are desirably dicarboxylic acids or anhydrides thereof or an aromatic acid having from about 3 to about 30 carbon atoms. Desirably the aliphatic carboxylic acids have from about 3 to about 10 carbon atoms whereas the aromatic carboxylic acids have from about 8 or 10 to about 20 carbon atoms. Examples of such acids include succinic, glutaric, adipic, pimelic, suberic, azelaic, sebacic, dodecanoic, isophthalic, terephthalic cyclohexane dicarboxylic, and the like. The polyols generally have from 2 to about 15 carbon atoms and include ethylene glycol, propylene glycol, butanediol, pentanediol, hexanediol, dimethylpropane diol, cyclohexanedimethanol, decamethylene glycol, dodecamethylene glycol, and the like, with butanediol generally being desired.

Crosslinking is generally accomplished in a separate step by radical copolymerization with alkene monomers such as styrene, vinyl toluene, methyl methacrylate, triallyl cyanurate, diallyl phthalate, and the like.

Polyvinyl Esters

Suitable thermosettable polyvinyl esters are known to the art and to the literature and generally have the formula

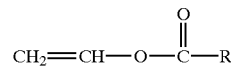

wherein R is an alkyl having from 1 to about 6 carbon atoms with vinyl acetate being preferred. The polyvinyl esters are generally made in the presence of catalyst such as mercuric salts as well as sulfuric acid. Such polymerization which can either be bulk, suspension, or emulsion is well known to the literature and to the art. Polyvinyl esters can be crosslinked according to a number of different methods as known to the literature and to the art. For example, suitable crosslinking agents include melamine, melamine-formaldehyde, urea-formaldehyde, and the like as through hydrolization of the ester group of the polyvinyl ester.

Cyanate Esters

Polycyanurates are known to the art and to the literature and are generally formed by the addition cyclotrimerization of —O—C≡N functional cyanate ester monomers and prepolymers. The formed network generally contains alternating triazine rings and bisphenol units connected by oxygen atoms. The —O— linkage is sterically an ether but electronically has ester character. Alternatively, the network can be considered a wholly aromatic ester derived from a bisphenol and cyanuric acid, i.e. polycyanurate. Desirably, the cyanate ester monomers are made by reacting bisphenols with cyanogen chloride in the presence of an HCl acceptor. Polymerization occurs via cyclotrimerization to polycyanurates but can also undergo thermal reversible additions to active hydrogen compounds and will co-react with epoxy functionality to form disubstituted oxazoline structures.

Epoxy (Meth)acrylates

Still another thermosetting polymer which can be utilized are the various epoxy (meth)acrylates known to the literature and to the art. These resin can be formed by reacting an epoxy resin, a carboxyl terminated elastomer and an unsaturated monocarboxylic acid such as acrylic or methacrylic acid. The preparation of such thermosetting resins as well as various reaction conditions thereof are set forth in U.S. Pat. No. 3,928,491 which is hereby fully incorporated by reference.

Generally the amount of toughener or adduct, such as set forth by Formula Z, is small based upon the amount of the polymer to be crosslinked and thus is generally from about 1 to about 20, and desirably from about 5 to about 15 by weight per 100 parts by weight of the polymer to be toughened, e.g. the epoxy resin.

In order to form crosslinked matrixes or compositions, curing agents are utilized. The equivalent weight ratio of the curing agent to the thermosettable resin, e.g. an epoxy resin, as well as the toughener or adduct is generally from about 0.25 to about 5.0, desirably from about 0.75 to about 1.25, and preferably from about 0.9 to about 1.1. Desirably, the toughener or adduct and the epoxy resin are mixed or blended before the curing agent is added thereto.

Suitable curing agents for the trithiocarbonate or epoxy terminated toughener or adduct, as well as for the thermoset polymer to be formed include amine curing agents, acid-anhydride curing agents, amide curing agents, nitrogen containing compounds, acid curing agents, latent curing agents, and the like.

Suitable amine curing agents are well known to the art and to the literature and include aliphatic diamines such as polymethylene diamines, polyether diamines, and branched-chain polymethylene diamines; linear and branched chain polyamines such as diethylenetriamine (DETA), iminobispropylamine, bis(hexamethylene) triamine, triethylenetetramine (TETA), TETA modified with epoxy resin or ethylene oxide, tetraethylenepentamine (TEPA), pentaethylenehexamine (PEHA), aminoethylethanolamine,dimethylaminopropylamine, diethylaminopropyla mine (DEAPA), methylaminobispropylamine, substituted 1,2-diamines, and substituted polyamines; alicyclic polyamines such as menthane diamine, N-aminoethylpiperazine (AEP), 1,3-diaminocyclohexane, and isophoronediamine; aliphatic amines containing aromatic groups such as m-xylylenediamine, and tetrachloro-p-xylenediamine; aromatic primary amines such as m-phenylenediamine (MPDA), and 4–4'-methylenedianilene (MDA); linear and branched aliphatic tertiary amines such as tetramethylguamidene, triethanolamine, N,N,N',N'-tetraethyl-1,3-butenediamine, 2-dimethylamino-2-hydroxypropane, linear diamines, dialkyl aminoethanols, and alkyl tertiary monoamines; alicyclic tertiary amines such as N-N'-dimethylpiperazine, N-methylmorpholine, hexamethylenetetramine,N,N-bis[(2-hydroxy)propyl] piperazine, and 1,4-diazabicyclo(2.2.2)octane (triethylenediamine); unsaturated-ring tertiary amines such as 1-hydroxyethyl-2-heptadicylgloxalidene, pyrazine, pyridene, and quinoline; aromatic ring-containing aliphatic tertiary amines such as benzyldimethylamine, 2-(dimethylaminomethyl)phenol(DMP-10), .alpha.-methylbenzyldimethylamine, and 2,4,6-tris (dimethylaminomethyl)phenol (DMP-30); tertiary amine salts such as tri-2-ethylhexoate salt of DMP-30, quaternary bases such as benzyltrimethylammonium chloride; secondary amines such as N-methylpiperazine, piperidine, morpholine, hydroxyethylpiperazine, pyrrolidine, and anabasine.

Amides can also be used as curing agents in epoxy resin systems and include amidopolyamines, imidazoline polyamines, and fatty polyamides. Amidopolyamines are frequently selected as the curing agent in two-part epoxy resin systems.

Miscellaneous nitrogen-containing compounds can also be used as curing agents in epoxy resin systems and include urea, urea-formaldehyde, and substituted ureas; melamines and other s-triazine-type curing agents such as melamines including melamine and N,N-diallylmelamine and other guanamines, melamineformaldehyde resins, hexamethoxymethyl-melamine, triallylcyanurate, and cyanuric chloride; imidazoles such as 2-ethyl-4-methylimidazole; hydrazides such as carbohydrazide and adipic acid dihydrazide; guanidines such as tetramethylguanidine and heptamethylisoguanidine; nitrosamines such as ethylenically unsaturated alpha,beta-nitrosamines; ethylene amines such as polyalkylene imines; thioureas such as polythioureas, and sulfonamides.

Acid curing agents suitable for epoxy resin systems include Lewis acids such as $BF_3$ piperidine; phenolics such as novolac resins and resole resins; inorganic acids such as phosphoric acid; and organic acids.

Acid-anhydride curing agents suitable for either the carboxyl terminated toughener or the epoxy resins include linear aliphatic anhydrides such as polysebacic polyanhydride (PSPA) and polyazelaic polyanhydride (PAPA); alicyclic anhydrides such as succinic anhydride, citraconic anhydride, itaconic anhydride, dodecyenylsuccinic anhydride, tricarbalylic anhydride, maleic anhydride, linoleic acid adduct of maleic anhydride, copolymer of maleic anhydride and vinyl ether, copolymer of maleic anhydride and styrene, maleic anhydride adduct of methylcyclopentadiene, alkylated endoalkylene-tetrahydrophthalic anhydride, dimethyl-substituted butenyltetrahydrophthalic anhydride, methyltetrahydrophthalic anhydride, and hexahydrophthalic anhydride (HHPA), and alkenyl anhydrides; multi-ring alicyclic dianhydrides such as bis nadic anhydrylbutene; aromatic anhydrides such as phthalic anhydride, trimellitic anhydride, pyromellitic dianhydride (PMDA), PMDA in blends with monoanhydrides, PMDA in solvents, PMDA-glycol adducts, and PMDA dispersions; chlorinated and brominated anhydrides such as dichloromaleic anhydride and chlorendic anhydride.

Latent curing agents which are suitable for use in thermoset epoxy resin systems used in the present invention include many commercially available curing agents which are well-known to the art and to the literature. Some desirable curing agents include solid polyamides such as HT-939 which is manufactured by Ciba-Geigy Corporation; $BF_3$ monoethylamine ($BF_3$ MEA); and diaminodiphenylsulfone (DDS).

In addition, to the various above set forth curing agents, various amine-terminated polyethers can be utilized which are often exemplified by the various Jeffamines produced by Huntsman Chemical. One group of amine-terminated polyethers are represented by the formula

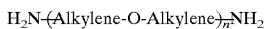

can be utilized where n is an integer from about 2 to about 100, desirably from about 2 to about 70 and preferably from about 2 to about 5, and wherein each "Alkylene", independently, has from about 2 to about 10 carbon atoms with 2 carbon atoms, that is ethylene, or 3 carbon atoms, that is propylene, being preferred. The "Alkylene" group can be branched or straight. Specific examples of such amine terminated polyethers include the Jeffamine D-Series and have the formula

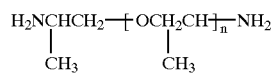

where n is an integer of from about 2 to about 100.
The various types of available Jeffamine D-Series products where n is an integer of from about 2 to about 100, include the following

| Product | n | Approx. Mol. Wt. |
|---|---|---|
| Jeffamine D-230 | 2–3 | 230 |
| Jeffamine D-400 | 5–6 | 400 |
| Jeffamine D-2000 | 33 | 2000 |
| Jeffamine D-4000 | 68 | 4000 |

Other types of amine terminated polyethers suitable for use are represented by the formula

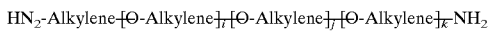

wherein each "Alkylene," independently, is set forth above, and wherein i plus k is an integer of from about 2 to about 25, desirably from about 2 to about 10 and preferably from about 2 to about 5. The number of repeating units represented by j is an integer of from about 1 to about 200, desirably from about 2 to about 150 and preferably from about 2 to about 10. Examples of such suitable polyethers include the Jeffamine ED-Series and have the formula

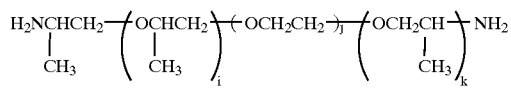

Examples of such specific Jeffamine ED-Series polymers include the following:

| Product | j | i + k | Approx. Mol. Wt. |
|---|---|---|---|
| Jeffamine ED-6008 | 8.5 | 2.5 | 600 |
| Jeffamine ED-900 | 15.5 | 2.5 | 900 |
| Jeffamine ED-2001 | 40.5 | 2.5 | 2,000 |
| Jeffamine ED-4000 | 86.0 | 2.5 | 4,000 |
| Jeffamine ED-6000 | 31.5 | 2.5 | 6,000 |

Still another type of suitable amine terminated polyethers which can be utilized are those generally represented by the formula

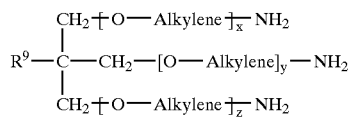

wherein each "Alkylene," independently, is as set forth above, that is, has from about 2 to about 10 carbon atoms therein with 2 or 3 carbon atoms being preferred. The total number of x+y+z integers is from about 2 to about 100, desirably from about 2 to about 10 and preferably from about 5 to about 10. $R^9$ is hydrogen or an aliphatic group with a desirable aliphatic group being an alkyl. When $R^9$ is an alkyl it has from about to about 5 carbon atoms with 1 or 2 carbon atoms being preferred. Examples of such suitable polyethers include the Jeffamine T-Series which have the formula:

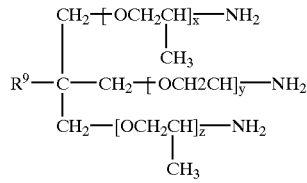

Examples of such specific Jeffamine T-Series include the following:

| Product | Approx. Value x + y + z | Approx. Mol. Wt. |
|---|---|---|
| Jeffamine T-403 | 5–6 | 440 |
| Jeffamine T-3000 | 50 | 3000 |
| Jeffamine T-5000 | 85 | 5000 |

Once the epoxy terminated toughener or adduct has been mixed with the epoxy resin and blended with the curing agent and an optional catalyst, the composition is formed into any desirable shape such as a sheet, a coating on a substrate, a molded part, a laminate, or the like and cured either at room temperature, 15° C. and higher, or at elevated temperatures such as from about 50° C. to about 200° C. and preferably from about 80° C. to about 130° C. Elevated temperatures of course reduce curing time. The epoxy resin is desirably in liquid form in order to promote mixing of the various components as well as to maintain a low viscosity. Mixing of the epoxy terminated toughener or adduct with the curing agent with subsequent addition and mixing of the epoxy resin is generally undesirable inasmuch as carboxylic amine salts are generally formed as a biproduct which unacceptably increase the viscosity of the epoxy resin-toughener system before cure. During cure, the various different types of curing agents will react with the terminal epoxy groups on the toughener as well as the terminal epoxy groups of the epoxy resins per se. Since the equivalent weight ratio of the curing agent to the epoxy resin as well as the toughener is approximately one to one and since each amine group, amide group, etc., of the curing agent can react, a number of reactions occur wherein a crosslinked network is formed. As noted above, in lieu of the epoxy terminated toughener, the carbonate toughener can be utilized.

The invention will be better understood by reference to the following examples which serve to illustrate, but not to limit, the present invention.

Examples 1 through 11 generally relate to the preparation of s,s'-bis-(α,α'—disubstituted—α"—acetic acid)—trithiocarbonate and polymers thereof such as described by Formula W.

EXAMPLE 1

Synthesis of s,s'-bis-(α,α'—disubstituted—α"—acetic acid)—trithiocarbonate, ($R^1=R^2=CH_3$)

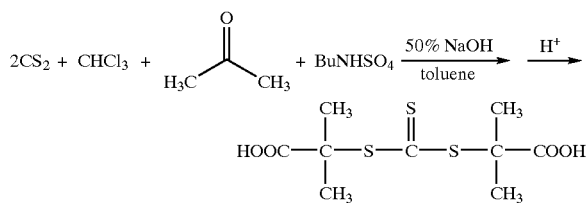

Procedure

In a 500 ml jacketed flask equipped with a mechanical stirrer, a thermometer, a reflux condenser and an addition funnel added 22.9 grams of carbon disulfide, 2.0 gram of tetrabutylammonium bisulfate and 100 ml toluene. The solution was stirred at 20° C. under nitrogen and 168 grams of 50% sodium hydroxide solution was added dropwise to keep the temperature between 20–30° C. 30 min. after the addition, a solution of 43.6 grams of acetone and 89.6 grams of chloroform was added at 20–30° C. The reaction was then stirred at 15–20° C. overnight. 500 ml water was added to the mixture, the layers were separated. The organic layer was discarded and the aqueous layer was acidified with concentrated HCl to precipitate the product as yellow solid. 50 ml toluene was added to stir with the mixture. Filtered and rinsed the solid with toluene to collect 22.5 grams of product after drying in the air to constant weight.

EXAMPLE 2

Synthesis of s,s'-bis-(α,α'—disubstituted—α"—acetic acid)—trithiocarbonates. ($R^1=R^2=CH_3$)

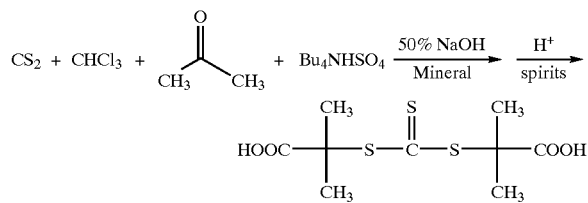

The procedure was essentially the same as in example 1, except that mineral spirits replaced toluene as solvent. 40.3 grams of product was obtained as yellow solid.

EXAMPLE 3

Synthesis of s-alkyl-s'-(-(α,α'—disubstituted—α"—acetic acid)—trithiocarbonates

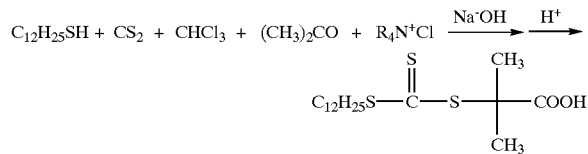

Procedure

Dodecylmercaptan (0.1 mole), and Aliquot 336 (0.004 mole) was dissolved in 48 g acetone. 50% sodium hydroxide solution (0.105 mole) was added, followed by dropwise addition of carbon disufide (0–1 mole) in 10 g acetone solution. The media turned from colorless to yellow. After 20 min., chloroform (0.5 mole) was added followed by dropwise addition of 50% NaOH (0.5 mole) and 5 g NaOH beads. The reaction was stirred at 15–20° C. overnight, filtered and the sol. was rinsed with acetone. The acetone layer was concentrated to dryness. The mass was dissolved in water, acidified with concentrated HCl to precipitate the product, rinsed with water to collect the yellow solid. The solid was dissolved in 350 ml of hexane. The solution was dried over magnesium sulfate and filtered. The organic solution was cooled to precipitate the product as yellow flakes. Yield is 85%.

EXAMPLE 4

Polymerization of Prior Art Compounds

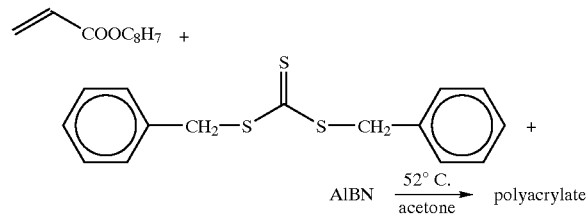

Procedure

Dibenzyltrithiocarbonate (1.54 g, 5.3 mmole), 2-ethylhexylacrylate (25 grams 135.7 mmole), AIBN (0.05 g, 0.3 mmole) and acetone (25 ml) were mixed. 1 ml of undecane was added as GC internal standard for calculating the conversion. The solution was purged with nitrogen for 15 min. before heating to 52° C. under nitrogen. No exotherm was detected throughout the reaction. Aliquots of the sample were taken for GC and GPA analyses during the course of the polymerization. The following table showed the progress of the polymerization in 7 hours.

| Sample | Time (mins.) | Mn | Mw | Conv. % |
|---|---|---|---|---|
| 1 | | | | |
| 2 | 120 | 866 | 970 | 3.7 |
| 3 | 270 | 1180 | 1428 | 13.2 |
| 4 | 420 | 1614 | 2059 | 26.9 |

EXAMPLE 5

Polymerization with s,s'-bis-(α,α'—disubstituted—α"—acetic acid)—trithiocarbonates

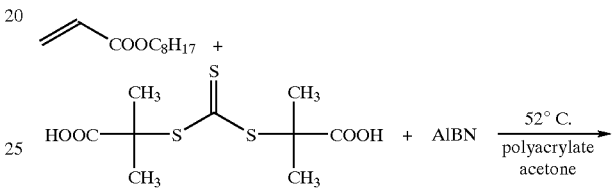

Procedure

Following the same procedure as in example 4, the novel tricarbonate (1.50 g, 5.3 mmole), 2-ethylhexylacrylate (25 g, 135.7 mmole), AIBN (0.05 g, 0.3 mmole) and acetone (25 ml) were mixed. 1 ml of undecane was added as internal standard. The reaction was stirred at 52° C. for 7 hours. The following table showed the conversion and the molecular weights of the resulting polymer.

| Sample | Time (mins.) | Mn | Mw | Conv. % |
|---|---|---|---|---|
| 1 | 45 | 669 | 724 | 3.5 |
| 2 | 120 | 1433 | 1590 | 25.8 |
| 3 | 240 | 3095 | 3621 | 79.8 |
| 4 | 300 | 3345 | 3898 | 87.9 |
| 5 | 420 | 3527 | 4136 | 93.9 |

EXAMPLE 6

Polymerization with s,s'-bis-(α,α'—disubstituted—α"—acetic acid)trithiocarbonates

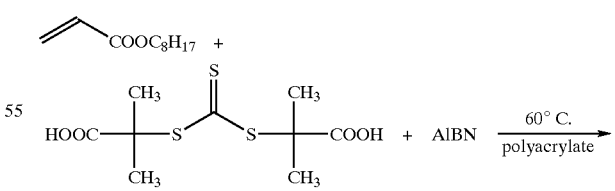

Procedure

This is a bulk polymerization with the trithiocarbonate as chain-transfer agent The trithiocarbonate (1.0 g, 3.5 mmole), 2-ethylhexylacrylate (25 g, 135.7 mmole), AIBN (0.05 g, 0.3 mmole) and 1 ml undecane (internal standard) were purged with nitrogen, then heated to 60° C. for 3 hours. The following table showed the conversion and the molecular weight of the polymer.

| Sample | Time (mins.) | Mn | Mw | Conv. % |
|---|---|---|---|---|
| 1 | 30 | 2229 | 2616 | 35.6 |
| 2 | 90 | 4501 | 5526 | 91.9 |
| 3 | 180 | 4672 | 5780 | 97.8 |

EXAMPLE 7

Polymerization with s,s'-bis-(α,α'—disubstituted—α"—acetic acid)trithiocarbonates

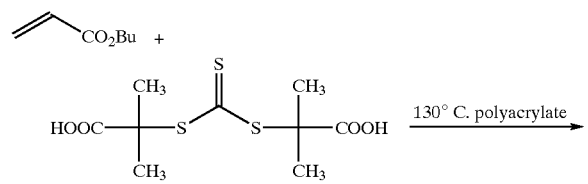

Procedure

The trithiocarbonate was used as inifertor. Trithiocarbonate (1.0 g, 3.5 mmole), n-butylacrylate (20 g, 156.1 mmole) with 1 ml decane as internal standard were purged with nitrogen for 15 min., then polymerized at 130° C. under nitrogen for 6 hours. The following table showed the conversion and the molecular weights of the polymer.

| Sample | Time (mins.) | Mn | Mw | Conv. % |
|---|---|---|---|---|
| 1 | 60 | 1118 | 1242 | 16.0 |
| 2 | 120 | 1891 | 2199 | 32.5 |
| 3 | 240 | 2985 | 3337 | 52.5 |
| 4 | 360 | 3532 | 4066 | 65.7 |

EXAMPLE 8

Free Radical Polymerization Utilizing s,s'-bis-(α,α'—disubstituted—α"—acetic acid)—trithiocarbonates as Inifertor

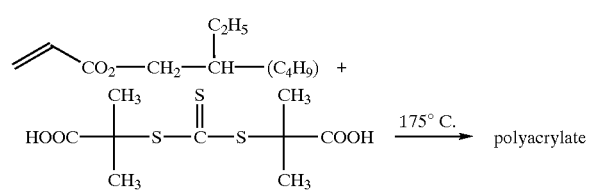

Procedure

The trithiocarbonate (2.0 g, 7.1 mmole) and 2-ethylhexylacrylate (25.0 g, 135.7 mmole) were purged with nitrogen for 15 min then heated to 175° C. for 10 hours. The following table showed the conversion and molecular weighs of the polymer.

| Sample | Time (mins.) | Mn | Mw | Conversion |
|---|---|---|---|---|
| 1 | 40 | 1006 | 1117 | 24.2 |
| 2 | 90 | 1446 | 1699 | 42.0 |

-continued

| Sample | Time (mins.) | Mn | Mw | Conversion |
|---|---|---|---|---|
| 3 | 150 | 1750 | 2241 | 51.9 |
| 4 | 600 | 2185 | 3115 | 98.9 |

EXAMPLE 9

Polymerization with s,s'-bis-(α,α'—disubstituted—α"—acetic acid)trithiocarbonates

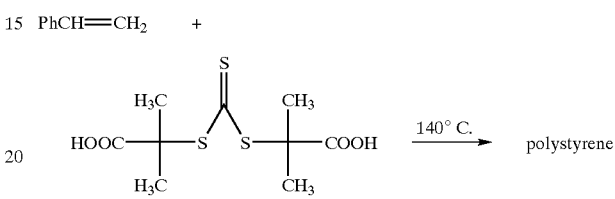

Procedure

The trithiocarbonate was used as inifertor to make polystyrene. The trithiocarbonate (2.0 g, 7.1 mmole) and styrene (25 g, 240.4 mmole) with 1 ml decane as internal standard were polymerized at 140° C. under nitrogen for 6 hours. The following table showed the progress of the polymerization.

| Sample | Time (mins.) | Mn | Mw | Conv. % |
|---|---|---|---|---|
| 1 | 30 | 613 | 648 | 9.5 |
| 2 | 60 | 779 | 831 | 16.9 |
| 3 | 120 | 1829 | 2071 | 53.9 |
| 4 | 300 | 2221 | 2559 | 72.3 |
| 5 | 360 | 2537 | 2956 | 84.5 |

EXAMPLE 10

Polymerization with s,s'-bis-(α,α'—disubstituted—α"—acetic acid)trithiocarbonates

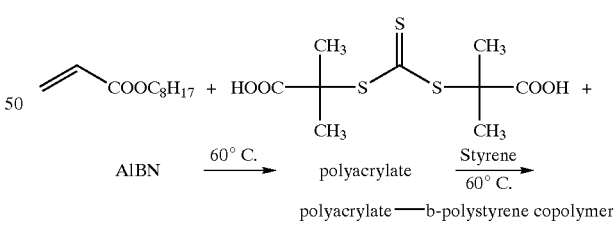

Procedure

The trithiocarbonate was used as chain-transfer agent to make block copolymers of 2-ethylhexylacrylate and styrene. The trithiocarbonate (1.5 g, 5.3 mmole), 2-ethylhexylacrylate (30 g, 162.8 mmole) and AIBN (0.03 g, 0.18 mmole) with 1 ml undecane as the internal standard were polymerized at 60° C. under nitrogen as before. 6.5 hours later, styrene (15 g, 144.2 mmole) and AIBN (0.03 g, 0.18 mmole) was added. The polymerization continued and the following shows the progress.

| Sample | Time (mins.) | Mn | Mw | Conv. % |
|---|---|---|---|---|
| 1 | 70 | 1922 | 2459 | 32.5 |
| 2 | 135 | 3556 | 4204 | 80.8 |
| 3 | 270 | 4095 | 4874 | 95.0 |
| 4 | 330* | 4407 | 5025 | 96.6 |
| 5 | 1290 | 4834 | 5969 | — |

*Styrene added

EXAMPLE 11

Polymerization with the trithiocarbonate from example 3. The trithiocarbonate (1.82 g, 5 mmole), n-butyl acrylate (25 g, 195.1 mmole) and AIBN (0.04 g, 0.25 mmole) with 1 ml undecane as the internal standard were polymerized under nitrogen atmosphere for 7 hours. It showed 97.5% conversion by GC as depicted in the following table:

| Sample | Time (min) | Mn | Mw | Pd | % Conv. |
|---|---|---|---|---|---|
| 1 | 60 | 2177 | 2792 | 1.26 | 46.2 |
| 2 | 120 | 2758 | 3865 | 1.40 | 67.1 |
| 3 | 420 | 3786 | 5439 | 1.44 | 97.5 |

Toughened Epoxy Resins with ETA

In the following examples, commercially available tougheners such as an epoxy-terminated butadiene-acrylonitrile liquid polymer which is commercially available from Resolution as ETBN 58006, as a comparison. Similar toughening properties were obtained between the ETBN 58006 and the tougheners of the present invention, i.e. ETA-1 through ETA-12.

Preparation of Epoxy-terminated Acrylates (ETA)

Example ETA-1

In a neat system, utilizing a flask prepared for polymerization, 125 grams butyl acrylate, 125 grams of ethyl acrylate, 0.05 grams of ADVA and 5.87 grams of trithiocarbonate were purged with nitrogen. Subsequently, a nitrogen needle was raised above the contents to provide a nitrogen blanket. Polymerization was allowed to occur at temperatures of from about 80° C. to about 90° C. for a total of approximately 10 hours. Epoxy resin (Epon 828) was then added to the polymer (in a 60/40 weight ratio epoxy/polymer) with triphenylphosphine (0.01 wt %) at 95° C. for 1 to 3 hours, leading to the adduct formation. Typical physical properties of ETA-1 is set forth herein below.

In a manner similar to Example 1, various other epoxy-terminated acrylates were made such as Examples ETA-7 and 9 wherein the amounts of the various components are set forth in Table A.

Example ETA-2

In a 250 ml flask equipped for polymerization, 48 grams of butyl acrylate, 12 grams of ethyl acrylate, 0.1 gram of AIBN, and 1.01 grams of trithiocarbonate were purged with a needle and placed in the solution containing EPON 828 as a solvent for at least 15 minutes. The needle was then raised to provide a nitrogen blanket. Polymerization was subsequently conducted at a temperature of about 80° C. for 3 to 8 hours. Epoxy resin (Epon 828) was then added to the polymer (in a 60/40 weight ratio epoxy/polymer) with triphenylphosphine (0.01 wt %) at 95° C. for 1 to 3 hours, leading to the adduct formation. The characterization properties for ETA-2 is set forth herein below.

In a similar manner, a solution system polymerization was conducted with regard to ETA-3–6, ETA-8, and ETA-10–12 with the amounts of the various components thereof set forth in Table A.

TABLE A

| | Parts by Weight of Components | | | |
|---|---|---|---|---|
| Product number | Butyl Acrylate Monomer | Ethyl Acrylate Monomer | TTC | Catalyst |
| ETA-1 | 125 | 125 | 5.87 | ADVA 0.05 |
| ETA-2 | 48 | 12 | 1.01 | AIBN 0.1 |
| ETA-3 | 50 | 50 | 1.76 | AIBN 0.03 |
| ETA-4 | 108 | 12 | 3.38 | AIBN 0.12 |
| ETA-5 | 80 | 80 | 2.82 | AIBN 0.048 |
| ETA-6 | 36 | 84 | 2.48 | AIBN 0.2 |
| ETA-7 | 250 | 0 | 9.4 | ADVA 0.05 |
| ETA-8 | 60 | 0 | 1.41 | AIBN 0.1 |
| ETA-9 | 250 | 0 | 7.2680 | AIBN 0.03 |
| ETA-10 | 20 | 20 | 0.05 | AIBN 0.02 |
| ETA-11 | 30 | 30 | 2.35 | ADVA 0.13 |
| ETA-12 | 45 | 15 | 10.01 | AIBN 0.1 |

The above recipes were polymerized in a manner noted with regard to Examples ETA-1 and ETA-2 characterization properties as set forth in the following table.

| Typical Charcterization Properties of ETAs | | | | | |
|---|---|---|---|---|---|
| Product Number | Monomer | Composition (wt. %) | Molecular weight ($M_w$) | Poly-dispersity | Function-ality |
| ETA-1 | BA/EA | 50/50 | 13500 | 1.06 | 2 |
| ETA-2 | BA/EA | 80/20 | 17000 | 1.17 | 2 |
| ETA-3 | BA/EA | 50/50 | 16000 | 1.24 | 2 |
| ETA-4 | BA/EA | 90/10 | 11000 | 1.11 | 2 |
| ETA-5 | BA/EA | 50/50 | 17000 | 1.07 | 2 |
| ETA-6 | BA/EA | 30/70 | 15000 | 1.12 | 2 |
| ETA-7 | BA | 100 | 8200 | 1.08 | 2 |
| ETA-8 | BA | 100 | 13000 | 1.14 | 2 |
| ETA-9 | BA | 100 | 11000 | 1.13 | 2 |
| ETA-10 | BA/EA | 50/50 | 11000 | 1.37 | 2 |
| ETA-11 | BA/EA | 50/50 | 8200 | 1.09 | 2 |
| ETA-12 | BA/EA | 75/25 | 18000 | 1.14 | 2 |

BA = Butyl Acrylate
EA = Ethyl Acrylate

EXAMPLE A

Anhydride Cured Epoxy Formulation

Blends of Epon 828 commercially available from Resolution, Nadic Methyl Anhydride (NMA) commercially available from Lonza Inc., an amine catalyst Ancamine K54, a hexanoic salt of 2,4,6-tris(dimethylamino methyl phenol), commercially available from Air Products, were formulated according to the following recipe. Various tougheners were added to the blends, such as epoxy-terminated butadiene-acrylonitrile liquid polymer (ETBN 58006) commercially available from Resolution and epoxy terminated polyacrylates (ETA) of the present invention. The ingredients were thoroughly mixed, degassed, poured into molds and cured in an oven at 95° C. for 2 hours, 150° C. for 2 hours and 177° C. for 0.5 hour. Plaques were cut into samples of various configurations required for ASTM testing methods. The physical properties are reported in the following table.

In the following tables, the most significant changes occurred in the critical strain energy release rate, or fracture energy, $G_{I_c}$ and the stress intensity factor $K_{I_c}$. These quantities are related by the following equation for plane strain conditions:

$$G_{Ic} = \frac{K_{Ic}^2(1-v^2)}{E}$$

where v=Poisson's ratio, and E=Young's modulus.

From this equation one can see that increases in fracture energy, $G_{I_c}$, of a material require an increase in $K_{I_c}$ with increasing amount of polymer so that any increases in $G_{I_c}$ cannot be attributed to a large decrease in modulus.

|  | Ingredients (phr) | | | | |
|---|---|---|---|---|---|
| Formulation | 1 | 2 | 3 | 4 | 5 |
| Epon 828 | 100 | 85 | 85 | 85 | 85 |
| NMA | 80 | 80 | 80 | 80 | 80 |
| Ancamine 2 | 2 | 2 | 2 | 2 |  |
| K54 |  |  |  |  |  |
| 58006 |  | 25 |  |  |  |
| ETA-1 |  |  | 25 |  |  |
| ETA-2 |  |  |  | 25 |  |
| ETA-3 |  |  |  |  | 25 |
| Plastic flexural properties ASTM D790-95a | | | | | |
| Stress at yield (psi) | 19100 | 17700 | 16200 | 15900 | 17200 |
| Std Dev. | 658 | 127 | 1530 | 762 | 213 |
| Strain at yield (in/in) | 0.075 | 0.070 | 0.061 | 0.060 | 0.066 |
| Std. Dev. | 0.002 | 0.002 | 0.016 | 0.010 | 0.002 |
| Modulus (kpsi) | 400 | 389 | 375 | 368 | 372 |
| Std. Dev. | 16 | 7 | 2 | 5 | 16 |
| Plane-Strain Fracture Toughness ASTM D5045-96 | | | | | |
| $K_{1c}$ (MPa · m$^{0.5}$) | 0.55 | 1.15 | 1.16 | 1.18 | 1.25 |
| Std. Dev. | 0.04 | 0.04 | 0.14 | 0.05 | 0.05 |
| $G_{1c}$ (J/m$^2$) | 148 | 436 | 460 | 485 | 539 |
| Std. Dev. | 1 | 1 | 7 | 1 | 1 |
| Tg (DSC) ° C. | 154 | 148 | 149 | 152 | 150 |

The results obtained indicated a significant increase of the fracture toughness upon the addition of various ETA adducts. The tensile properties remained relatively unchanged upon the addition of the toughener. A slight decrease of Tg is observed upon addition of the tougheners.

EXAMPLE B

Anhydride Cured Epoxy Formulation

In a manner similar than in Example 1, blends of Epon 828 commercially available from Resolution, Methyltetrahydrophtalic Anhydride (MTHPA) commercially available from Lonza Inc., benzyldimethylamine catalyst (BDMA) commercially available from Lonza Inc., were formulated according to the following recipe. Various tougheners were added to the blends, such as epoxy-terminated butadiene-acrylonitrile liquid polymer (ETBN 58006) commercially available from Resolution and various epoxy-terminated polyacrylates (ETA). The ingredients were thoroughly mixed, degassed, poured into molds and cured in an oven at 90° C. for 1 hour and at 150° C. for 4 hours. Plaques were cut into samples of various configurations required for ASTM testing methods. The mechanical properties are reported in the following table.

|  | Ingredients (phr) | | | | |
|---|---|---|---|---|---|
| Formulation | 1 | 2 | 3 | 4 | 5 |
| Epon 828 | 100 | 85 | 85 | 85 | 85 |
| MTHPA | 80 | 80 | 80 | 80 | 80 |
| BDMA | 1 | 1 | 1 | 1 | 1 |
| 58006 |  | 25 |  |  |  |
| ETA-4 |  |  | 25 |  |  |
| ETA-5 |  |  |  | 25 |  |
| ETA-6 |  |  |  |  | 25 |

-continued

| | Ingredients (phr) | | | | |
|---|---|---|---|---|---|
| Formulation | 1 | 2 | 3 | 4 | 5 |
| Plastic flexural properties ASTM D790-95a | | | | | |
| Stress at yield (psi) | 19600 | 18000 | 17200 | 15800 | 17400 |
| Std Dev. | 947 | 96 | 291 | 1120 | 373 |
| Strain at yield(in/in) | 0.060 | 0.063 | 0.061 | 0.055 | 0.060 |
| Std. Dev. | 0.010 | 0.001 | 0.005 | 0.01 | 0.004 |
| Modulus (Kpsi) | 442 | 395 | 392 | 369 | 390 |
| Std. Dev. | 8 | 5 | 10 | 20 | 4 |
| Plane-Strain Fracture Toughness ASTM D5045-96 | | | | | |
| $K_{1c}$ (MPa·$m^{0.5}$) | 0.57 | 1.22 | 1.04 | 1.26 | 1.09 |
| Std. Dev. | 0.10 | 0.06 | 0.03 | 0.04 | 0.09 |
| $G_{1c}$ (J/$m^2$) | 95 | 483 | 354 | 552 | 390 |
| Std. Dev. | 3 | 1 | 1 | 1 | 2 |
| Tg (DSC) °C. | 126 | 123 | 122 | 127 | 125 |

The results obtained indicated a significant increase of the fracture toughness upon the addition of various ETA adducts. The tensile properties remained relatively unchanged upon the addition of the toughener. A slight decrease or no change of Tg is observed upon addition of the tougheners.

EXAMPLE C
IPDA-cure Epoxy Formulations

In a similar manner than in Example 1, blends of Epon 828 commercially available from Resolution and isophorone diamine (Aradure 2963) commercially available from Vantico Inc., were formulated according to the following recipe. Various tougheners were added to the blends, such as epoxy-terminated butadiene-acrylonitrile liquid polymer (ETBN 58005) commercially available from Resolution and various epoxy-terminated polyacrylates (ETA). The ingredients were thoroughly mixed, degassed, poured into molds, cured at room temperature for 4 hours and in an oven at 100° C. for 1 hour. Plaques were cut into samples of various configurations required for ASTM testing methods. The physical properties are reported in the following table.

| | Ingredients (phr) | | | | | |
|---|---|---|---|---|---|---|
| Formulation | 1 | 2 | 3 | 4 | 5 | 6 |
| Epon 828 | 100 | 85 | 85 | 85 | 85 | 85 |
| Aradur 2963 | 45 | 45 | 45 | 45 | 45 | 45 |
| 58005 | | 25 | | | | |
| ETA-7 | | | 25 | | | |
| ETA-8 | | | | 25 | | |
| ETA-5 | | | | | 25 | |
| ETA-1 | | | | | | 25 |
| Plastic flexural properties ASTM D790-95a | | | | | | |
| Stress at yield (psi) | | 12100 | 11600 | 11200 | 12000 | 11700 |
| Std Dev. | | 171 | 47 | 197 | 66 | 109 |
| Strain at yield (in/in) | | 0.053 | 0.051 | 0.052 | 0.051 | 0.052 |
| Std. Dev. | | 0.001 | 0.001 | 0.001 | 0.0004 | 0.0007 |
| Modulus (Kpsi) | | 363 | 356 | 357 | 367 | 354 |
| Std. Dev. | | 9 | 1 | 6 | 6 | 6 |
| Plane-Strain Fracture Toughness ASTM D5045-96 | | | | | | |
| $K_{1c}$ (Mpa·$m^{0.5}$) | | 1.92 | 1.95 | 2.39 | 2.07 | 1.99 |
| Std. Dev. | | 0.22 | 0.06 | 0.02 | 0.1 | 0.14 |
| $G_{1c}$ (J/$m^2$) | | 1309 | 1370 | 2045 | 1493 | 1434 |
| Std. Dev. | | 17 | 1 | 1 | 4 | 7 |
| Tg (DSC) °C. | | 108 | 100 | 124 | 104 | 111 |

The results obtained indicated a significant increase of the fracture toughness upon the addition of various ETA adducts. The tensile properties remained relatively unchanged upon the addition of the toughener.

EXAMPLE D
Polyamide-cured Epoxy Formulation

In a manner similar than in Example 1, blends of Epon 828 commercially available from Resolution and polyamide Ancamide 501 commercially available from Air Products were formulated according to the following recipe. Various tougheners were added to the blends, such as epoxy-terminated butadiene-acrylonitrile liquid polymer (ETBN 58006) commercially available from Resolution and various epoxy-terminated polyacrylates (ETA). The ingredients were thoroughly mixed, degassed, poured into molds and cured at room temperature for 2 hours and at 177° C. for 0.5 hour. Plaques were cut into samples of various configurations required for ASTM testing methods. The physical properties are reported in the following table.

adducts. The tensile properties remained relatively unchanged upon the addition of the toughener. A slight decrease or no change of Tg is observed upon addition of the tougheners.

EXAMPLE E
Polymeric Amine-cured Epoxy Formulation

In a manner similar than in Example A, blends of Epon 828 commercially available from Resolution and Jeffamine D230 commercially available from Hunstman were formulated according to the following recipe. Various tougheners were added to the blends, such as epoxy-terminated butadiene-acrylonitrile liquid polymer (ETBN 58006) commercially available from Resolution and various epoxy-terminated polyacrylates (ETA). The ingredients were thoroughly mixed, degassed, poured into molds and cured at 80° C. for 2 hours and at 125° C. for 3 hours. Plaques were cut into samples of various configurations required for ASTM

|  | Ingredients (phr) | | | | |
|---|---|---|---|---|---|
| Formulation | 1 | 2 | 3 | 4 | 5 |
| Epon 828 | 100 | 85 | 85 | 85 | 85 |
| Ancamide 501 | 35 | 35 | 35 | 35 | 35 |
| 58006 |  | 25 |  |  |  |
| ETA-9 |  |  | 25 |  |  |
| ETA-5 |  |  |  | 25 |  |
| ETA-10 |  |  |  |  | 25 |
| Plastic flexural properties ASTM D790-95a | | | | | |
| Stress at yield (psi) | 15100 | 14000 | 13700 | 13600 | 13,306 |
| Std Dev. | 1090 | 445 | 243 | 492 | 442 |
| Strain at yield (in/in) | 0.057 | 0.075 | 0.073 | 0.066 | 0.065 |
| Std. Dev. | 0.011 | 0.009 | 0.001 | 0.01 | 0.005 |
| Modulus (Kpsi) | 368 | 317 | 313 | 342 | 322 |
| Std. Dev. | 12 | 10 | 13 | 5 | 10 |
| Plane-Strain Fracture Toughness ASTM D5045-96 | | | | | |
| $K_{1c}$ (MPa·m$^{0.5}$) | 0.81 | 1.09 | 1.11 | 1.06 | 1.09 |
| Std. Dev. | 0.06 | 0.03 | 0.08 | 0.07 | 0.09 |
| $G_{1c}$ (J/m$^2$) | 230 | 480 | 419 | 344 | 464 |
| Std. Dev. | 1 | 1 | 3 | 1 | 2 |
| Tg (DSC) ° C. | 97 | 95 | 96 | 96 | 96 |

The results obtained indicated a significant increase of the fracture toughness upon the addition of various ETA testing methods. The physical properties are reported in the following table.

|  | Ingredients (phr) | | | | |
|---|---|---|---|---|---|
| Formulation | 1 | 2 | 3 | 4 | 5 |
| Epon 828 | 100 | 85 | 85 | 85 | 85 |
| Jeffamine D230 | 30 | 30 | 30 | 30 | 30 |
| 58006 |  | 25 |  |  |  |
| ETA-9 |  |  | 25 |  |  |
| ETA-11 |  |  |  | 25 |  |
| ETA-12 |  |  |  |  | 25 |

-continued

| | Ingredients (phr) | | | | |
|---|---|---|---|---|---|
| Formulation | 1 | 2 | 3 | 4 | 5 |
| Plastic flexural properties ASTM D790-95a | | | | | |
| Stress at yield (psi) | 15600 | 12600 | 13000 | 14600 | 12700 |
| Std Dev. | 169 | 126 | 202 | 532 | 520 |
| Strain at yield (in/in) | 0.059 | 0.064 | 0.055 | 0.052 | 0.057 |
| Std. Dev. | 0.001 | 0.008 | 0.001 | 0.001 | 0.001 |
| Modulus (Kpsi) | 421 | 352 | 370 | 410 | 363 |
| Std. Dev. | 29 | 10 | 14 | 24 | 14 |
| Plane-Strain Fracture Toughness ASTM D5045-96 | | | | | |
| $K_{1c}$ (MPa · $m^{0.5}$) | 0.91 | 3.06 | 2.80 | 2.90 | 2.76 |
| Std. Dev. | 0.02 | 0.26 | 0.25 | 0.11 | 0.17 |
| $G_{1c}$ (J/$m^2$) | 253 | 3411 | 2717 | 2630 | 2691 |
| Std. Dev. | 1 | 25 | 21 | 10 | 10 |
| Tg (DSC) ° C. | 81 | 83 | 80 | 72 | 70 |

The results obtained indicated a significant increase of the fracture toughness upon the addition of various ETA adducts. The tensile properties remained relatively unchanged upon the addition of the toughener. A slight decrease or no change of Tg is observed upon addition of the tougheners.

The epoxy resins of the present invention which have been toughened can be utilized wherever such properties are desired with improved oxidation and UV stability. Numerous uses exist as known to the art and to the literature. Some end uses include adhesives, composites, coatings, sealants, caulks, potting resins, foams, laminates, and the like.

While in accordance with the patent statutes the best mode and preferred embodiment have been set forth, the scope of the invention is not limited thereto, but rather by the scope of the attached claims.

What is claimed is:

1. A composition comprising:
a polymer having the formula

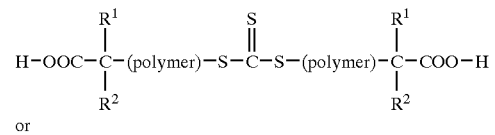

or

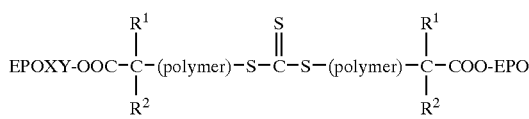

wherein $R^1$ and $R^2$, independently, is a linear or branched alkyl having from 1 to about 6 carbon atoms, or a substituted $C_1$ to about $C_6$ alkyl having one or more substituents, or aryl, or a substituted aryl having from 1 to 6 substituents on the aryl ring; wherein said one or more substituents, independently, represent an alkyl having from 1 to about 6 carbon atoms, or an aryl, or a halogen which can be the same different, or a cyano, or an ether having a total of from 2 to about 20 carbon atoms, or a nitro; or wherein $R^1$ and $R^2$ are part of a ring having from about 5 to about 12 total carbon atoms;
wherein said (polymer), independently, is derived from a conjugated diene monomer containing from 4 to about 12 carbon atoms, or is derived from a vinyl monomer having the formula

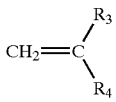

wherein $R^3$ is selected from hydrogen, halogen, $C_1$ to $C_4$ alkyl, or substituted $C_1$–$C_4$ alkyl wherein the substituents, independently, comprise one or more hydroxy, alkoxy, arloxy($OR^5$), carboxy, acyloxy, aryloxy($O_2CR^5$), alkoxy-carbonyl($CO_2R^5$), or aryloxy-carbonyl; wherein $R^4$ is selected from hydrogen, $R^5$, $CO_2H$, $CO_2R^5$, $COR^5$, CN $CONH_2$, $CONHR^5$, $O_2CR^5$, $OR^5$, or halogen; wherein $R^5$ is selected from $C_1$–$C_{18}$ alkyl, substituted $C_1$–$C_{18}$ alkyl, $C_2$–$C_{18}$ alkenyl, aryl, heterocyclyl, aralkyl, or alkaryl, wherein the substituents independently are selected from one or more epoxy, hydroxy, alkoxy, acyl, acyloxy, carboxy (and salts), sulfonic acid (and salts), alkoxy- or aryloxy-carbonyl, dicyanato, cyano, silyl, halo and dialkylamino; or wherein said (polymer), independently, is derived from maleic anhydride, N-vinyl pyrrolidone, N-alkylmaleimide, N-arylmaleimide, dialkyl fumarate a cyclo- polymerizable monomer; styrene, α-methyl styrene, $C_1$–$C_{12}$ alkyl styrene with substituent groups both either on the chain or on the ring, N,N-alkylacrylamide, or combinations thereof;
wherein said EPOXY is derived from glycidyl ethers of novolac resins; glycidyl ethers of mononuclear di- and trihydric phenols; glycidyl ethers of bisphenols; glycidyl ethers of polynuelear phenols; epoxy resin from diphenolic acid; glycidyl ethers of aliphatic polyols; glycidyl esters; glycidyl epoxies containing nitrogen; glycidyl derivatives of cyanuric acid; glycidyl amines; thioglycidyl resins; silicon-glycidyl resins; fluorine glycidyl resins; epoxy resins where are synthesized from monoepoxies other than epihalohydrins including epoxy resins from unsaturated monoepoxies; epoxy resins from monoepoxy alcohols; epoxy resins from monoepoxies by ester interchange; epoxy resins from glycidaldehyde; polyglycidyl compounds containing unsaturation; epoxy resins which are synthesized from olefins and chloroacetyls; or epoxy-resin adducts of the above, or combinations thereof.

2. A composition according to claim 1, wherein the number of repeat units in said (polymer) is from about 5 to about 10,000.

3. A composition according to claim 2, wherein said (polymer) is derived from ethyl acrylate, butyl acrylate, or ethyl-hexyl acrylate, or combinations thereof.

4. A composition according to claim 3, wherein the number of repeat units in said (polymer) is from about 5 to about 500.

5. A composition according to claim 2, wherein said (polymer) is a polyacrylate, and wherein the number of repeat units in said (polymer) is from about 10 to about 200.

6. A composition according to claim 5, wherein EPOXY is derived from

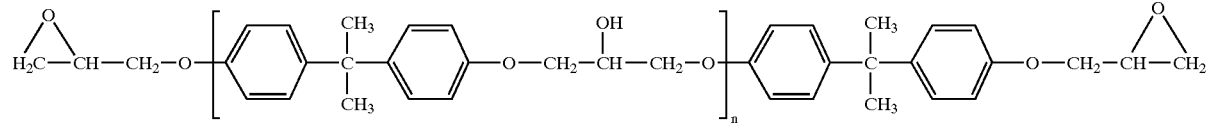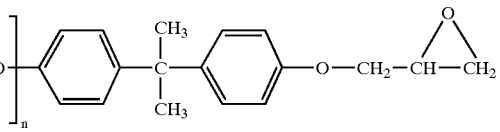

wherein n is an integer from 0 to about 18,
and wherein the number of said terminal EPOXY groups is 2.

7. A composition according to claim 6, wherein said (polymer) is derived from ethyl acrylate, butyl acrylate, or ethyl-hexyl acrylate, or combinations thereof.

8. A composition, comprising:
the reaction product of a polymer with an epoxy resin in the presence of an acid anhydride curing agent, wherein said polymer is represented by the formula

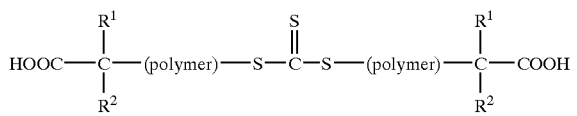

wherein $R^1$ and $R^2$, independently, is a linear or branched alkyl having from 1 to about 6 carbon atoms, or a substituted $C_1$ to about $C_6$ alkyl having one or more substituents, or aryl, or a substituted aryl having from 1 to 6 substituents on the aryl ring; wherein said one or more substituents, independently, represent an alkyl having from 1 to 6 carbon atoms, or an aryl, or a halogen which can be the same or different, or a cyano, or an ether having a total of from 2 to about 20 carbon atom, or a nitro; or wherein $R^1$ and $R^2$ are part of a ring having from about 5 to about 12 total carbon atoms; and
wherein said (polymer), independently, is derived from a conjugated diene monomer containing from 4 to about 12 carbon atoms, or is derived from a vinyl monomer having the formula

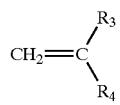

where $R^3$ is selected from hydrogen, halogen, $C_1$ to $C_4$ alkyl, or substituted $C_1$–$C_4$ alkyl wherein the substituents, independently, comprise one or more hydroxy, alkoxy, aryloxy($OR^5$), carboxy, acyloxy, aryloxy($O_2CR^5$), alkoxy-carbonyl($CO_2R^5$), or aryloxy-carbonyl; wherein $R^4$ is selected from hydrogen, $R^5$, $CO_2H$, $CO_2R^5$, $COR^5$, CN, $CONH_2$, $CONHR^5$, $O_2CR^5$, $OR^5$, or halogen; wherein $R^5$ is selected from $C_1$–$C_{18}$ alkyl, substituted $C_1$–$C_{18}$ alkyl, $C_2$–$C_{18}$ alkenyl, aryl, heterocyclyl, aralkyl, or alkaryl, wherein the substituents independently are selected from one or more epoxy, hydroxy, alkoxy, acyl, acyloxy, carboxy (and salts), sulfonic acid (and salts), alkoxy- or aryloxy-carbonyl, dicyanato, cyano, silyl, halo and dialkylamino; or wherein said polymer is derived from maleic anhydride, N-vinyl pyrrolidone, N-alkylmaleimide, N-arylmaleimide, dialkyl fumarate a cyclo-polymerizable monomer, styrene, α-methyl styrene, $C_1$–$C_{12}$ alkyl styrene with substituent groups both either on the chain or on the ring, N,N-alkylacrylamide, or combinations thereof.

9. A composition according to claim 8, wherein the number of repeat units in said (polymer) is from about 5 to about 500 and wherein said (polymer) is a polyacrylate.

10. A composition according to claim 9, wherein said polyacrylate is derived from ethyl acrylate, butyl acrylate, or ethyl-hexyl acrylate, or combinations thereof, and wherein the amount of said polymer is from about 1 to about 20 parts by weight per 100 parts by weight of said epoxy resin.

11. A composition according to claim 10, wherein the number of repeat units in said (polymer) is from about 5 to about 500.

12. A composition comprising:
the reaction product of a polymer with an epoxy resin in the presence of a curing agent, wherein said polymer is represented the formula

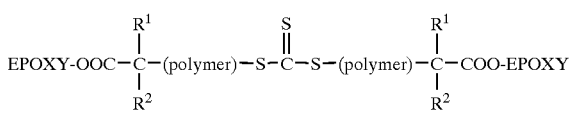

wherein $R^1$ and $R^2$, independently, is a linear or branched alkyl having from 1 to about 6 carbon atoms, or a substituted $C_1$ to about $C_6$ alkyl having one or more substituents, or aryl, or a substituted aryl having from 1 to 6 substituents on the aryl ring; wherein said one or more substituents, independently, represent an alkyl having from 1 to 6 carbon atoms, or an aryl, or a halogen which can be the same or different, or a cyano, or an ether having a total of from 2 to about 20 carbon atoms, or a nitro, or wherein $R^1$ and $R^2$ are part of a ring having from about 5 to about 12 total carbon atoms;

wherein said (polymer), independently, is derived from a conjugated diene monomer containing from 4 to about 12 carbon atoms, or is derived from a vinyl monomer having the formula

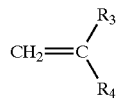

where $R^3$ is selected from hydrogen, halogen, $C_1$ to $C_4$ alkyl, or substituted $C_1$–$C_4$ alkyl wherein the substituents, independently, comprise one or more hydroxy, alkoxy, aryloxy($OR^5$), carboxy, acyloxy, aryloxy($O_2CR^5$), alkoxy-carbonyl($CO_2R^5$), or aryloxy-carbonyl; wherein $R^4$ is selected from hydrogen, $R^5$, $CO_2H$, $CO_2R^5$, $COR^5$, CN, $CONH_2$, $CONHR^5$, $O_2CR^5$, $OR^5$, or halogen; wherein $R^5$ is selected from $C_1$–$C_{18}$ alkyl, substituted $C_1$–$C_{18}$ alkyl, $C_2$–$C_{18}$ alkenyl, aryl, heterocyclyl, aralkyl, or alkaryl, wherein the substituents independently are selected from one or more epoxy, hydroxy, alkoxy, acyl, acyloxy, carboxy (and salts), sulfonic acid (and salts), alkoxy- or aryloxy-carbonyl, dicyanato, cyano, silyl, halo and dialkylamnino; or wherein said (polymer), independently, is derived from maleic anhydride, N-vinyl pyrrolidone, N-alkylmaleimide, N-arylmaleimide, dialkyl fumarate a cyclopolymerizable monomer; styrene, α-methyl styrene, $C_1$–$C_{12}$ alkyl styrene with substituent groups both either on the chain or on the ring, N,N-alkylacrylamide, or combinations thereof;

wherein said EPOXY is derived from glycidyl ethers of novolae resins; glycidyl ethers of mononuclear di- and trihydric phenols; glycidyl ethers of bisphenols; glycidyl ethers of polynuclear phenols; epoxy resin from diphenolic acid; glycidyl ethers of aliphatic polyols; glycidyl esters; glycidyl epoxies containing nitrogen; glycidyl derivatives of cyanuric acid; glycidyl amines; thioglycidyl resins; silicon-glycidyl resins; fluorine glycidyl resins; epoxy resins where are synthesized from monoepoxies other than epihalohydrins including epoxy resins from unsaturated monoepoxies; epoxy resins from monoepoxy alcohols; epoxy resins from monoepoxies by ester interchange; epoxy resins from glycidaldehyde; polyglycidyl compounds containing unsaturation epoxy resins which are synthesized from olefins and chloroacetyls; or epoxy-resin adducts of the above, or combinations thereof.

13. A composition according to claim 12, wherein said curing agent is an amine, an amide, an acid, an acid-anhydride, a nitrogen containing compound, or a latent curing catalyst, or an amine terminated polyether, or combinations thereof, and wherein the amount of said polymer is from about 1 to about 20 parts by weight per 100 parts by weight of said epoxy resin.

14. A composition according to claim 13, wherein the equivalent weight of said curing agent is from about 0.25 to about 5.0 based on the equivalent weight of said polymer and said epoxy resin, and wherein said (polymer) is a polyacrylate.

15. A composition according to claim 14, wherein said epoxy resin is

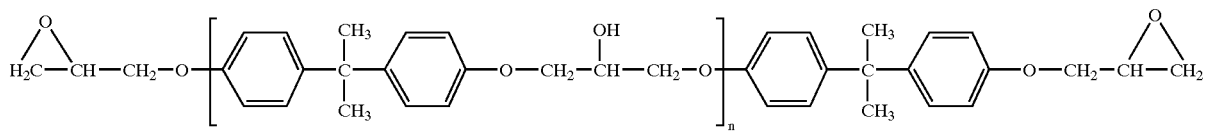

wherein n is an integer from 0 to about 18, and wherein said polyacrylate is derived from ethyl acrylate, butyl acrylate, or ethyl-hexyl acrylate, or combinations thereof.

16. A composition according to claim 15, wherein the amount of said polymer is from about 5 to about 15 parts by weight per 100 parts by weight of said epoxy resin.

17. A process for forming a thermoset composition, comprising the steps of:

mixing a polymer and an epoxy resin, said polymer having the formula

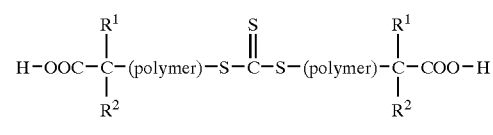

or

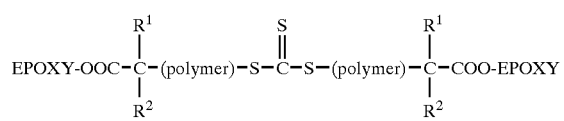

wherein $R^1$ and $R^2$, independently, is a linear or branched alkyl having from 1 to about 6 carbon atoms, or a substituted $C_1$ to about $C_6$ alkyl having one or more substituents, or aryl, or a substituted aryl having from 1 to 6 substituents on the aryl ring; wherein said one or more substituents, independently, represent an alkyl having from 1 to 6 carbon atoms, or an aryl, or a halogen which can be the same or different, or a cyano, or an ether having a total of from 2 to about 20 carbon atoms, or a nitro, or wherein $R^1$ and $R^2$ are part of a ring having from about 5 to about 12 total carbon atoms;

wherein said (polymer), independently, is derived from a conjugated diene monomer containing from 4 to about 12 carbon atoms, or is derived from a vinyl monomer having the formula

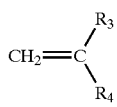

where $R^3$ is selected from hydrogen, halogen, $C_1$ to $C_4$ alkyl, or substituted $C_1$–$C_4$ alkyl wherein the substituents, independently, comprise one or more hydroxy, alkoxy, aryloxy($OR^5$), carboxy, acyloxy, aryloxy($O_2CR^5$), alkoxy-carbonyl($CO_2R^5$), or aryloxy-carbonyl; wherein $R^4$ is selected from hydrogen, $R^5$, $CO_2H$, $CO_2R^5$, $COR^5$, $CN$, $CONH_2$, $CONHR^5$, $O_2CR^5$, $OR^5$, or halogen; wherein $R^5$ is selected from $C_1$–$C_{18}$ alkyl, substituted $C_1$–$C_{18}$ alkyl, $C_2$–$C_{18}$ alkenyl, aryl, heterocyclyl, aralkyl, or alkaryl, wherein the substituents independently are selected from one or more epoxy, hydroxy, alkoxy, acyl, acyloxy, carboxy (and salts), sulfonic acid (and salts), alkoxy- or aryloxy-carbonyl, dicyanato, cyano, silyl, halo and dialkylamino; or wherein said (polymer), independently, is derived from maleic anhydride, N-vinyl pyrrolidone, N-alkylmaleimide, N-arylmaleimide, dialkyl fumarate a cyclo- polymerizable monomer; styrene, α-methyl styrene, $C_1$–$C_{12}$ alkyl styrene with substitute groups both either on the chain or on the ring, N,N-alkylacrylamide, or combinations thereof;

wherein said EPOXY is derived from glycidyl ethers of novolac resins; glycidyl ethers of mononuclear di- and trihydric phenols; glycidyl ethers of bisphenols; glycidyl ethers of polynuclear phenols; epoxy resin from diphenolic acid; glycidyl ethers of aliphatic polyols; glycidyl esters; glycidyl epoxies containing nitrogen; glycidyl derivatives of cyanuric acid; glycidyl amines; thioglycidyl resins; silicon-glycidyl resins; fluorine glycidyl resins; epoxy resins where are synthesized from monoepoxies other than epihalohydrins including epoxy resins from unsaturated monoepoxies; epoxy resins from monoepoxy alcohols; epoxy resins from monoepoxies by ester interchange; epoxy resins from glycidaldehyde; polyglycidyl compounds containing unsaturation; epoxy resins which are synthesized from olefins and chloroacetyls; or epoxy-resin adducts of the above, or combinations thereof.

18. A process according to claim 17, wherein said (polymer) is a polyacrylate, wherein said polyacrylate is derived from ethyl acrylate, buryl acrylate, or ethyl-hexyl acrylate, or combinations thereof; and wherein the amount of said polymer is from about 5 to about 15 parts by weight per 100 parts by weight of said epoxy resin.

19. A process according to claim 17, wherein said polymer end group is said H.

20. A process according to claim 18, wherein said polymer end group is said H.

21. A process according to claim 18, wherein said curing agent is an amine, an amide, an acid, an acid-anhydride, a nitrogen containing compound, or a latent curing catalyst, or an amine terminated polyether, or combinations thereof.

22. A process according to claim 21, wherein said epoxy resin, is

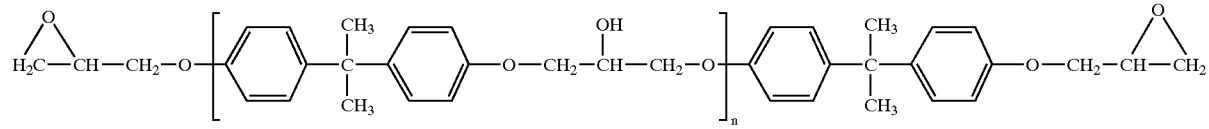

wherein n is an integer from 0 to about 18.

* * * * *